United States Patent
Ellering

(10) Patent No.: US 8,932,203 B2
(45) Date of Patent: *Jan. 13, 2015

(54) BODY IMPLANTABLE PENILE PROSTHETIC ASSEMBLY WITH ONE TOUCH TO ERECTION (OTTER) CAPABILITY AND PENILE IMPLANT DEFLATION CAPABILITY

(71) Applicant: Colopast A/S, Humlebaek (DK)

(72) Inventor: Nicholas Ellering, Crystal, MN (US)

(73) Assignee: Coloplast A/S, Humlebaek (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/027,246

(22) Filed: Sep. 16, 2013

(65) Prior Publication Data

US 2014/0012073 A1 Jan. 9, 2014

Related U.S. Application Data

(63) Continuation of application No. 13/195,869, filed on Aug. 2, 2011, now Pat. No. 8,568,294, which is a continuation of application No. 12/879,009, filed on Sep. 10, 2010, now Pat. No. 8,016,746, which is a continuation of application No. 12/699,891, filed on Feb. 4, 2010, now Pat. No. 8,545,393.

(30) Foreign Application Priority Data

Feb. 3, 2010 (DK) .................................. 2010 70035

(51) Int. Cl.
A61F 2/26 (2006.01)

(52) U.S. Cl.
CPC .......................................... *A61F 2/26* (2013.01)
USPC ........................................................... 600/40

(58) Field of Classification Search
USPC ................................. 600/38–41; 128/897, 898
See application file for complete search history.

(56) References Cited

U.S. PATENT DOCUMENTS 8,016,746 B2 * 9/2011 Ellering ............................ 600/40
8,568,294 B2 * 10/2013 Ellering ............................ 600/40

FOREIGN PATENT DOCUMENTS

FR 2556585 A1 6/1985
GB 1549315 A 8/1979

* cited by examiner

*Primary Examiner* — Samuel Gilbert
(74) *Attorney, Agent, or Firm* — Coloplast Corp., Coloplast A/S; Nick Baumann

(57) ABSTRACT

A body implantable penile prosthetic assembly offering a user a one touch to erection (OTTER) capability and a penile implant deflation capability is described. The assembly includes a pump and a release mechanism. The pump is connectable to a pressure reservoir and a penile implant. The pump is operable to pressurize liquid in the pressure reservoir and the pressure reservoir is operable to store the pressurized liquid at a first pressure between 20-50 PSIg that is configured to inflate the penile implant to an erect state. The release mechanism is connectable between the pressure reservoir and the penile implant. The release mechanism is operable to inflate the penile implant with one-touch input from the user where the release mechanism is configured to release the stored pressurized liquid from the pressure reservoir to inflate the penile implant at a second pressure between 10-20 PSIg.

14 Claims, 19 Drawing Sheets

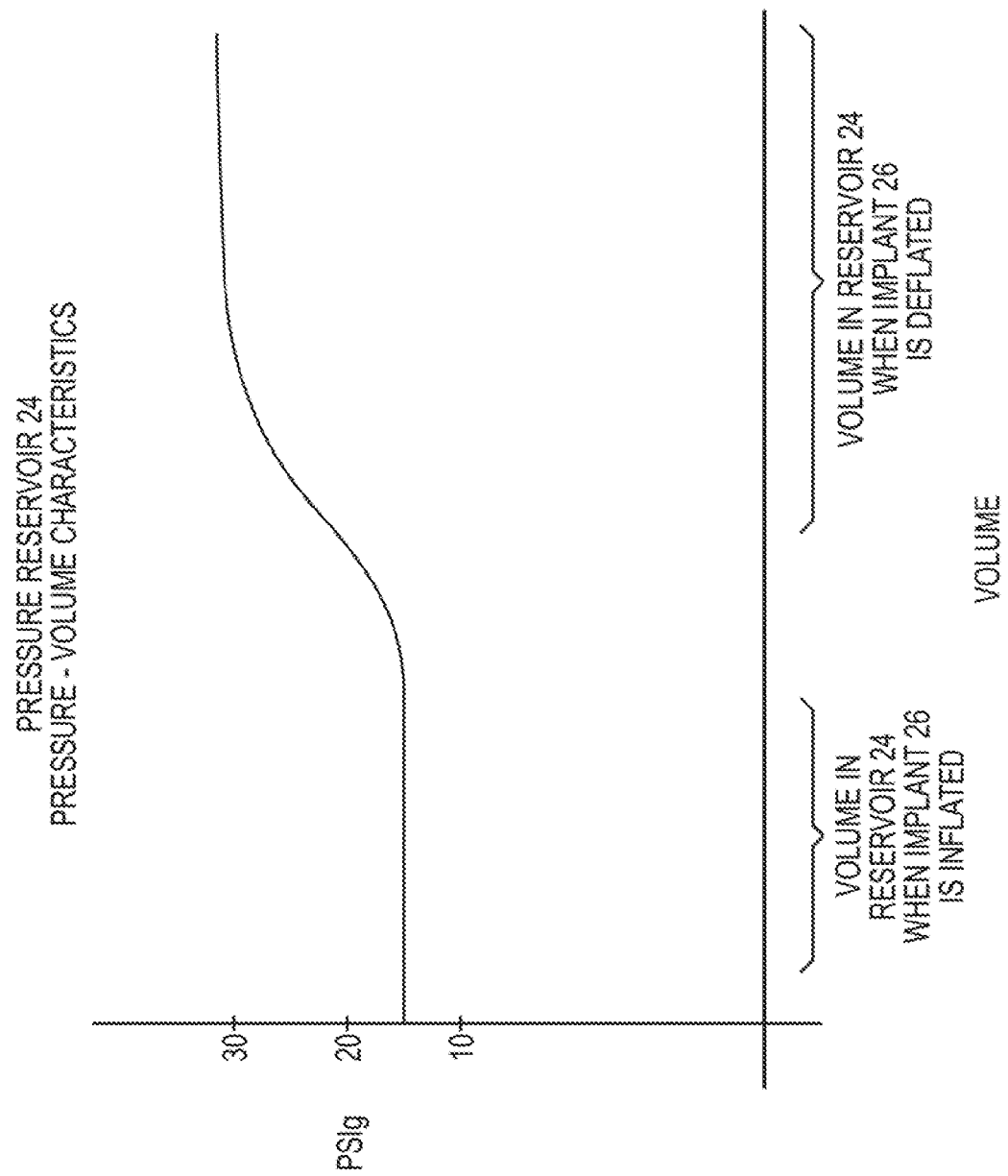

BODY IMPLANTABLE PENILE PROSTHETIC ASSEMBLY WITH ONE TOUCH TO ERECTION (OTTER) CAPABILITY AND PENILE IMPLANT DEFLATION CAPABILITY

BACKGROUND

An implanted penile prosthetic is effective in relieving erectile dysfunction in men.

A penile prosthetic typically includes one or more cylinders that are implanted in the corpora cavernosa of the penis, a liquid reservoir implanted in the abdomen that communicates with the cylinder(s), and a pump, often located in the scrotum, that is employed to move liquid from the liquid reservoir into the cylinder(s).

In a typical application, the user squeezes a bulb of the pump multiple times to incrementally draw liquid out of the liquid reservoir, into the bulb, and eventually into the cylinders. The repeated squeezing of the bulb moves the liquid from the reservoir into the cylinders, which incrementally deflates the reservoir and incrementally inflates the cylinder(s) to eventually provide the user with an erect penis. The user may return the penis to its flaccid state by selectively transferring the liquid from the cylinder(s) back into the reservoir.

The above-described penile prosthetics have proven effective in relieving erectile dysfunction in men. However, men have expressed a continuing desire for more spontaneous, efficient, and effective penile prostheses.

SUMMARY

One aspect provides a body implantable penile prosthetic assembly including a pump and a release mechanism. The pump is connectable to a pressure reservoir and a penile implant, where the pressure reservoir contains a pressurized liquid at a first pressure when implanted. The release mechanism is connectable between the pressure reservoir and the penile implant and is configured to release the pressurized liquid from the pressure reservoir to inflate the penile implant to a second pressure that is less than the first pressure. The pump is operable to transfer the pressurized liquid from the penile implant to the pressure reservoir to deflate the penile implant, and pressurize the pressurized liquid in the pressure reservoir from the second pressure to at least the first pressure.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 8B is a schematic graph of pressure-volume characteristics of the pressure reservoir of the body implantable penile prosthetic assembly illustrated in FIG. 8A.

DETAILED DESCRIPTION

Figure 1:
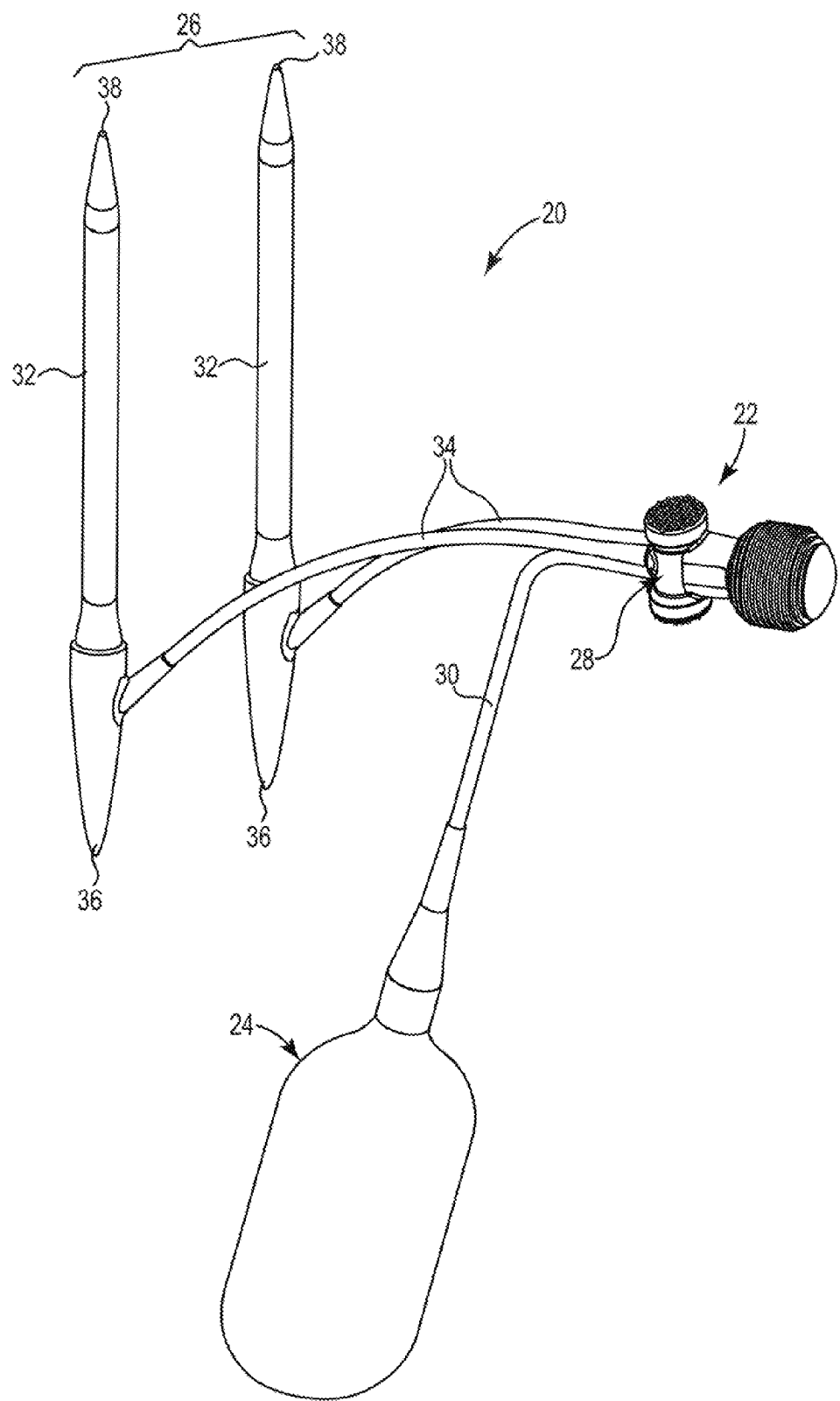
FIG. 1 is a perspective view of a body implantable penile prosthetic assembly including a pump connected to a pressure reservoir and a penile implant according to one embodiment.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

The term "proximal" as employed in this application means that the referenced part is situated next to or near the point of attachment or origin or a central point: as located toward a center of the human body. The term "distal" as employed in this application means that the referenced part is situated away from the point of attachment or origin or the central point: as located away from the center of the human body. A distal end is the furthest endmost location of a distal portion of a thing being described, whereas a proximal end is the nearest endmost location of a proximal portion of the thing being described. For example, the glans penis is located distal, and of the crus of the penis is located proximal relative to the male body such that a distal end of a corpora cavernosum of the patient extends about midway into the glans penis.

"Fluid" means a non-solid substance that flows and includes gases and liquids, or a combination of a gas and a liquid.

"Gas" means a substance having molecules that disperse and are free to expand to occupy an entire volume of a container in which it is disposed. Air and methyl butane are two examples of gases.

"Liquid" means a substance having molecules that do not disperse such that the liquid resists compression and the molecules of the liquid will not disperse to fill all spaces of a container in which the liquid is disposed. Saline is an example of a liquid.

"Immediate" in this Specification is employed in the context of inflating a penile implant and means that the implant is inflatable to an erect state in a time of less than about 5 seconds. Thus, an "immediately inflatable penile implant" is a penile implant that inflates in less than 5 seconds to provide the penis with an erection. In one embodiment, the penile implant inflates in about 2 seconds to provide the penis with nearly instantaneous erection.

Atmospheric pressure at sea level is approximately 14 pounds per square inch (PSI). The pressure measured or referred to as regards the pressurized liquid in the penile prosthetic assembly described herein is in reference to a gauge pressure, which is a pressure that has been increased above atmospheric pressure. This gauge pressure is recorded as pounds per square inch gauge (PSIg).

Embodiments provide a body implantable penile prosthetic assembly having a pressure reservoir that allows the implant to be immediately inflatable, or in other words, be inflatable with one-touch user input (sometimes referred to as "one-up" inflatable). In one embodiment, the pressure reservoir is pressurized prior to intimate relations and a release mechanism that releases pressurized liquid from the pressure reservoir to immediately inflate the penile implant for a more natural and spontaneous erection of the penis.

The prosthetic assembly of the embodiments described herein is configured to inflate the penile implant to an erect state within 5 seconds or so, which stands in stark contrast to the known prosthetic assemblies that become incrementally erect over a time frame from one-half to several minutes. The pressure reservoir is configured to be pressurized above atmospheric pressure, and the pump is configured to increase the pressure in the pressure reservoir; thus, the pressure in the pressure reservoir is not constant, but is user-adjustable to prepare for expected relations in cases where an immediate erection of the penis is desirable. In such cases, the increased pressure in the pressure reservoir is released to the implant via the release mechanism.

FIG. 1 is a perspective view of a penile prosthetic assembly 20 according to one embodiment. The penile prosthetic assembly 20 includes a pump 22 connected to a pressure reservoir 24 and a penile implant 26, and a release mechanism 28 connected between the pressure reservoir 24 and the penile implant 26. Generally, the pump 22 is implanted into the scrotum of the user, the pressure reservoir 24 is implanted within the abdomen of the user, and the implant 26 is implanted within the penis.

In one embodiment, the penile prosthetic assembly 20 is implanted as a sealed system with the reservoir 24 pressurized to an initial pressure above atmospheric pressure, for example between 20-30 PSIg, and connected in a sealed manner to the other components of the assembly 20. The release mechanism 28 is configured to release the pressurized liquid from the pressure reservoir 24 to inflate the penile implant 26 to a pressure between 10-20 PSIg, which is less than the initial pressure. In one embodiment, for example, the reservoir 24 pressurized to an initial pressure between 20-29 PSIg to inflate the penile implant 26 to a pressure of 15 PSIg. That is to say the system of the implanted assembly 20 is not a constant pressure system, but the reservoir 24 is instead configured to be pressure-adjustable by the user to provide an inflation pressure that is sufficient to inflate the implants 26. When the implant 26 is inflated, the reservoir 24 and the implant 26 are pressurized to an equilibrium pressure in the range of 10-20 PSIg.

The pump 22 is operable to transfer the pressurized liquid from the penile implant 26 back to the pressure reservoir 24 to deflate the penile implant and also to pressurize the pressurized liquid in the pressure reservoir 24 back to between 20-30 PSIg. The pump 22 increases pressure in a liquid that is contained in the pressure reservoir 24 and the release mechanism 28 releases pressurized liquid from the pressure reservoir 24 to the penile implant 26 at a pressure that is configured to make the penile implant 26 erect.

The increased pressure in the pressure reservoir 24 can be maintained for several hours. The increased pressure in the pressure reservoir 24 is releasable on demand via the release mechanism 28 to transfer the pressurized liquid from the pressure reservoir 24 to the implant 26, which will result in the rapid inflation of the implant 26 to an erect state. As a point of reference in FIG. 1, the pressure reservoir 24 is illustrated in a pressurized state that is "primed" to immediately inflate the flaccid implant 26 upon activation of the release mechanism 28.

The pressure reservoir 24 is connected to the pump 22 via kink resistant tubing 30 and contains a liquid and such as water or saline. In one embodiment, the assembly 20 is hermetically sealed (i.e., the pump 22 does not pump air) with a sufficient amount of liquid in the reservoir 24 to inflate the implant 26 without undesirably accessing the assembly 20 to inject more liquid. The pump 22 is operable to increase the pressure of the liquid in the sealed pressure reservoir 24, and the pressure reservoir 24 is configured to expand and provide a pressurized system configured to immediately inflate the penile implant 26 on command from the user. In one embodiment, the pressure reservoir 24 is a flexible bladder having walls that expand as the liquid in the pressure reservoir 24 is pressurized. The expanded walls of the pressure reservoir 24 store potential energy for subsequent release to the implant 26.

Figure 13:
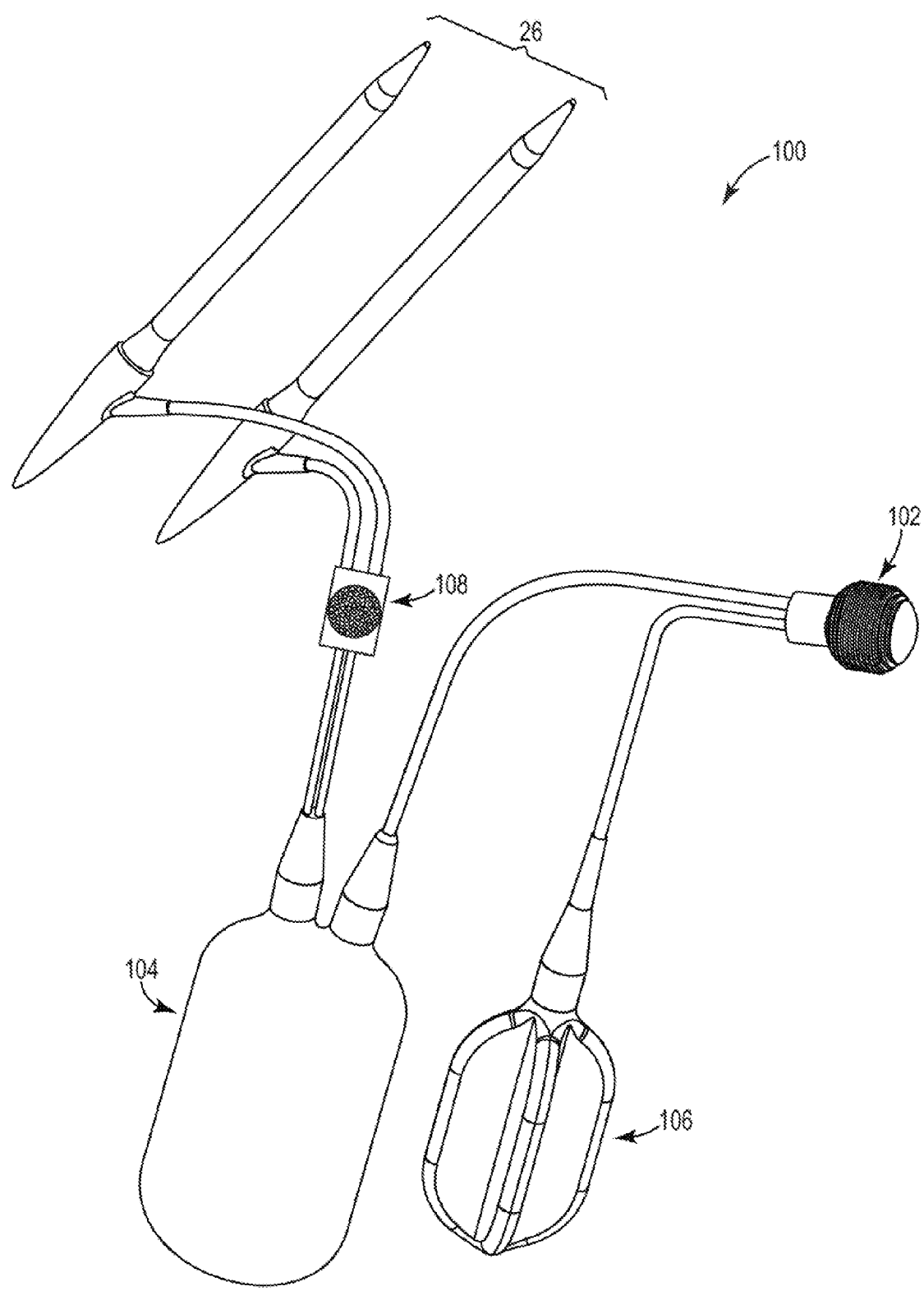
FIG. 13 is a perspective view of the body implantable penile prosthetic assembly illustrated in FIG. 9 with the pressure reservoir pressurized according to one embodiment.

The pressure reservoir 24 is sized to hold a volume of liquid between about 50-350 ml. In one embodiment, the pressure reservoir 24 is provided as a cylindrical reservoir formed from an elastic, flexible polymer with a wall thickness of between 0.010-0.060 inches. One exemplary embodiments of the reservoir 24 has a wall thickness of about 0.025 inches thick, formed of a polyurethane polymer, and so configured to have walls that expand to store potential energy created when the pump 22 increases the pressure of the liquid in the pressure reservoir 24. In one embodiment, the reservoir 24 is provided as a "cloverleaf" style of reservoir (as illustrated in FIG. 13) having multiple leaves that may be folded one against the other to compactly fold the pressure reservoir 24 for implantation into the abdomen of the user. One suitable reservoir 24 is sized to contain approximately 130 ml of liquid and is available from Coloplast Corp., Minneapolis, Minn.

In one embodiment, the penile implant 26 includes a pair of inflatable cylinders 32 that are sized to be implanted into the penis, and each of the cylinders 32 is connected to the pump 22 by kink resistant tubes 34. Each of the cylinders 32 includes a proximal end 36 opposite a distal end 38. During implantation, the proximal end 36 (also called a rear tip) is implanted toward the crus of the penis and the distal end 38 is implanted within the glans penis. The cylinders 32 are fabricated from material configured to collapse and be flexible when the cylinders 32 are deflated to provide the penis with a flaccid state and expand when the cylinders 32 are inflated with liquid to provide the penis with an erection. Suitable material for fabricating the cylinders 32 includes silicone, polymers such as urethanes, blends of polymers with urethane, copolymers of urethane, or the like. Suitable cylinders are available from Coloplast Corp., Minneapolis, Minn.

Figure 2:
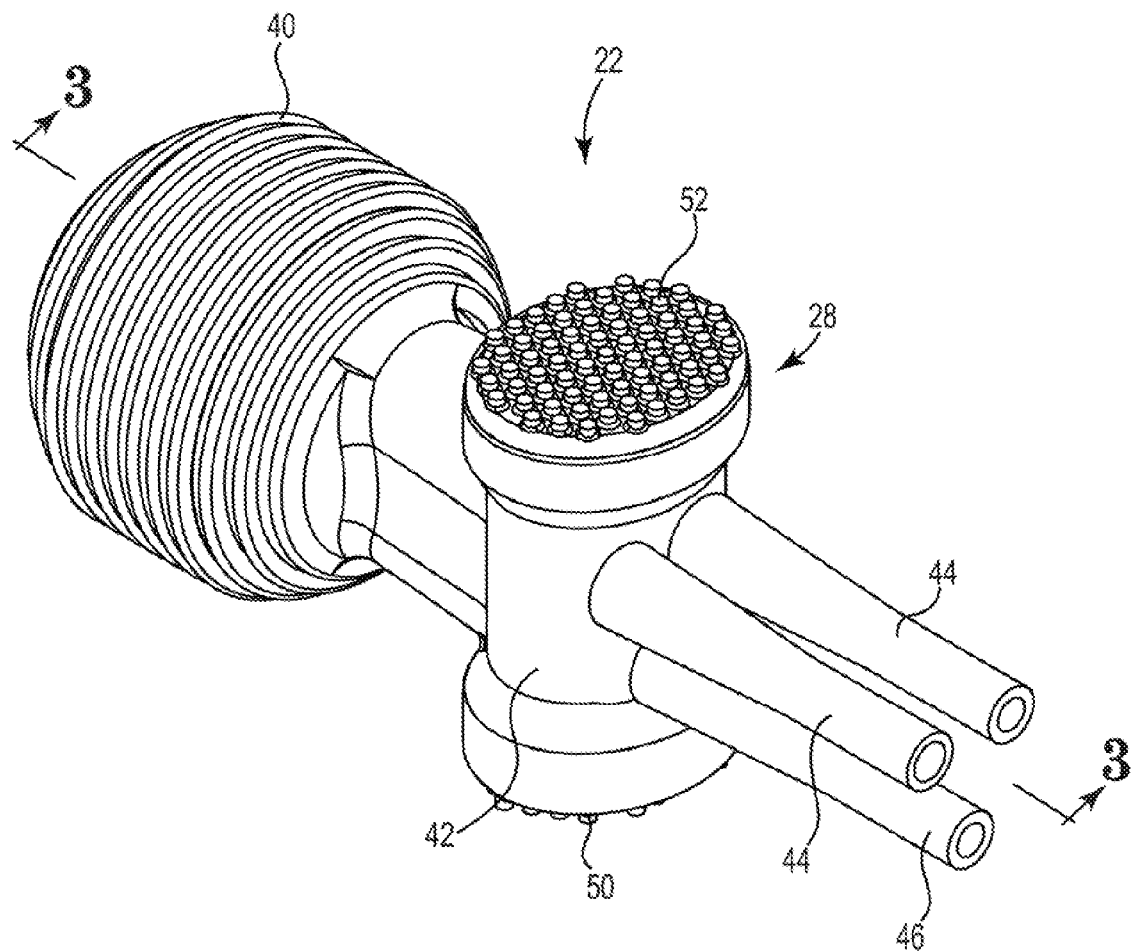
FIG. 2 is a perspective view of the pump illustrated in FIG. 1.

FIG. 2 is a perspective view of the pump 22. The pump 22 includes a pump bulb 40 connected to a pump body 42 that houses the release mechanism 28. The pump body 42 has a pair of inflation ports 44 that connect with the cylinders 32 via the tubes 34 (FIG. 1), and an exhaust port 46 that connects with the pressure reservoir 24 via the tube 30. The pump 22 is fabricated from material suitable for body implantation, such as silicone or the urethane-based materials described above for the cylinders 32 or the reservoir 24.

In one embodiment, the release mechanism 28 is integrated within the pump body 42. The pump body 42 is deformable and includes a first touch pad 50 opposite a second touch pad 52. The touch pads 50, 52 may have a circular shape or a non-circular (e.g., elliptical) shape, and other shapes for the touch pads 50, 52 are also acceptable. The pump body 42 houses or maintains valves (described below) that are activated/deactivated by pressing one or both of the touch pads 50, 52. In one embodiment, the pads 50, 52 are configured for one-touch deformation of the pump body 42 such that finger pressure applied to one of the pads 50, 52 by the implant user deforms the pump body 42 to allow pressurized liquid to flow around one or more of the internal valves.

In one embodiment, the pump bulb 40 is flexible and includes a pleated accordion structure that allows the pump bulb 40 to collapse and recover. The pump bulb 40 is operable to drive liquid into the pressure reservoir 24, or further pressurize the liquid in the pressure reservoir 24, or deflate the implant 26. For example, the pump bulb 40 is configured to reversibly collapse and recover to move liquid through the pump 22 or to pressurize the liquid that has collected in the pressure reservoir 24. When the cylinders 32 are inflated, the pump bulb 40 is operable to pump the liquid from the inflated cylinders 32, through the pump body 42 and the pump bulb 40, out of the exhaust port 46 and back into the pressure reservoir 24.

Figure 3:
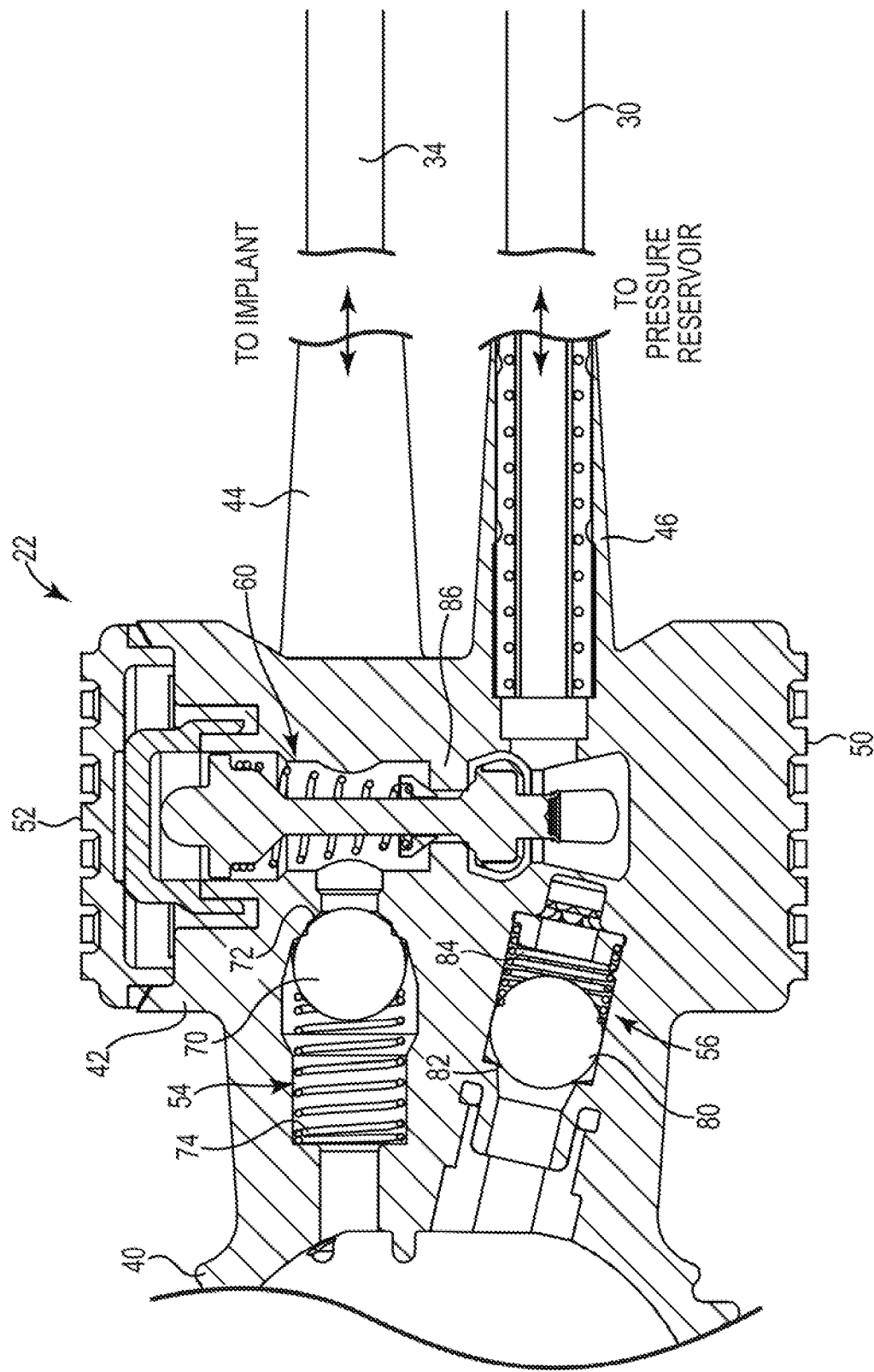
FIG. 3 is a cross-sectional view of the pump illustrated in FIG. 2 showing a release mechanism.

FIG. 3 is a cross-sectional view of the pump 22. With reference to FIG. 2, the cross-section of FIG. 3 has been taken through the pump body 42 between the two inflation ports 44. Thus, the inflation port 44 is in the background and is not shown in cross-section.

The pump 22 includes a deflation valve 54 disposed within the pump body 42 that communicates between the implant 26 (FIG. 1) and the pump bulb 40, an exhaust valve 56 disposed within the pump body 42 that communicates between the pump bulb 40 and the pressure reservoir 24, and a transverse valve 60 disposed in the pump body 42 between the deflation valve 54 and the exhaust valve 56. In one embodiment, the deflation valve 54 is aligned axially between the pump bulb 40 and the inflation ports 44, the exhaust valve 56 is aligned axially between the pump bulb 40 and the exhaust port 46, and the transverse valve 60 is transverse to the deflation valve 54 and the exhaust valve 56.

The deflation valve 54 includes a ball 70 that is biased into contact with a surface 72 by a spring 74. The ball 70 is configured to be displaced from the surface 72 (thus compressing the spring 74) when the pump bulb 40 applies suction, in which case liquid flows from the implant 26 through the inflation ports 44 and into the pump bulb 40. The spring 74 biases the ball 70 into contact with the surface to block the flow of the liquid from the pressurized implant 26 to the bulb 40. In this manner, the deflation valve 54 is a one-way valve.

The exhaust valve 56 includes a ball 80 that is biased into contact with a surface 82 by a spring 84. The ball 80 is configured to be displaced from the surface 82 (thus compressing the spring 84) when liquid is pushed from the pump bulb 40 through the exhaust valve 56 toward the pressure reservoir 24. For example, compressing the pump bulb 40 ejects liquid from the pump bulb 40, which unseats the ball 80 from the surface 82 to allow the liquid to flow past the ball 80 and the transverse valve 60 into the pressure reservoir 24. Repeatedly squeezing the pump bulb 40 will pressurize the liquid in the pressure reservoir 24. The spring 84 biases the ball 80 into contact with the surface 82 to block backflow of liquid from the pressure reservoir 24 into the pump bulb 40. In this manner, the exhaust valve 56 is provided as a one-way exhaust valve.

Figure 6:
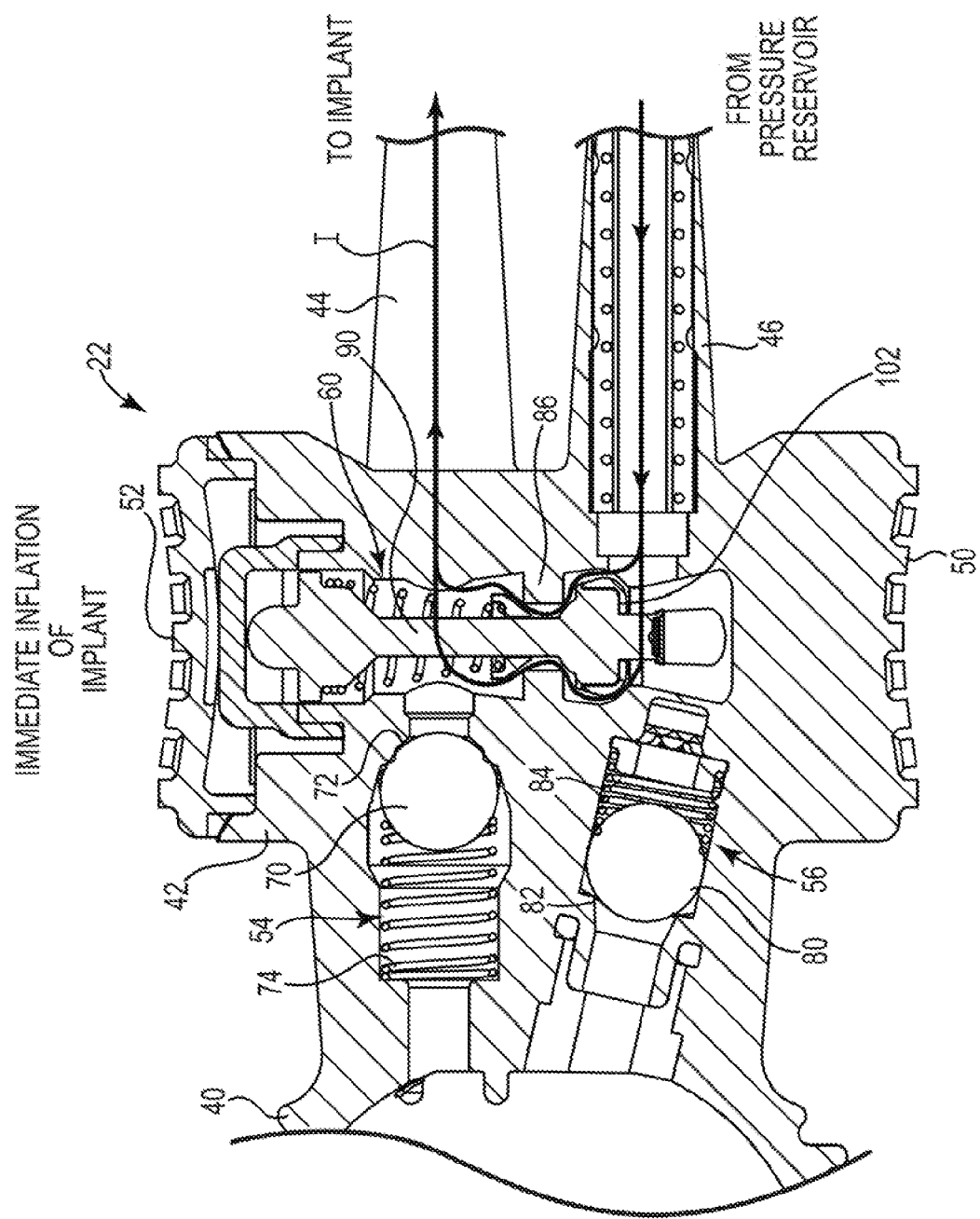
FIG. 6 is a cross-sectional view of the pump in a configuration for immediately inflating the penile implant illustrated in FIG. 1.

In one embodiment, the pump body 42 is an elastomeric chamber 86 molded around the transverse valve 60. The pump body 42 is deformable such that when the touch pads 50, 52 are squeezed, the chamber 86 molded around the transverse valve 60 is displaced away from the valve 60, which allows pressurized liquid to flow from the pressure reservoir 24 past the transverse valve 60 and into the cylinders 32 for immediate inflation of the cylinders (FIG. 6). In one embodiment, when the touch pads 50, 52 are squeezed, only the transverse valve 60 is "opened" (valves 54 and 56 are not opened) to allow the pressurized liquid to flow between the transverse valve 60 and the molded chamber 86 and into the cylinders 32 for immediate inflation of the cylinders. In one embodiment, the pump body 42 is silicone having a Shore-A hardness of between 10-65 Shore-A, for example.

Figures 4A, 4B:
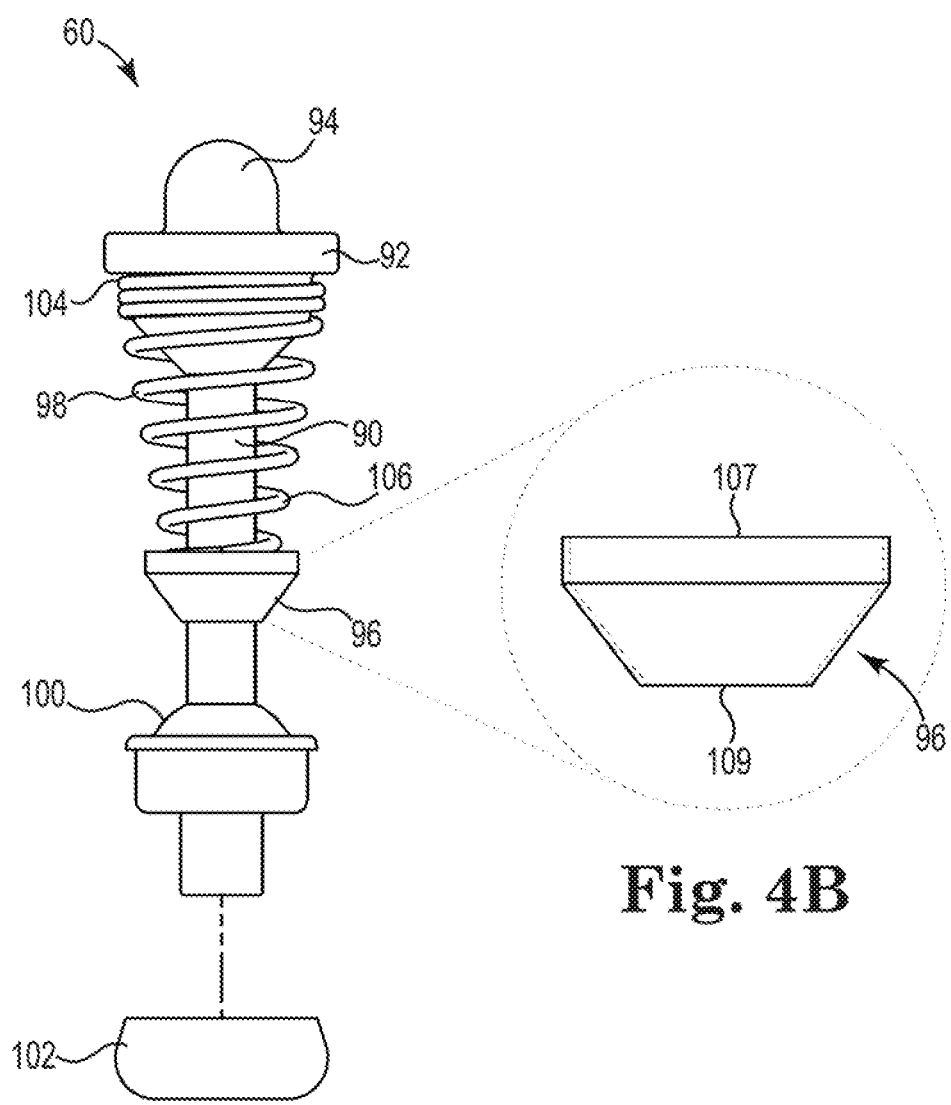
FIG. 4A is a side view of a transverse valve of the release mechanism illustrated in FIG. 3 according to one embodiment.
FIG. 4B is a side view of a seal of the release mechanism illustrated in FIG. 4A.

FIG. 4A is a side view of the transverse valve 60. The transverse valve 60 includes a valve stem 90, a flange 92 disposed on a first end of portion 94 of the valve stem 90, a seal 96, a spring 98 that biases the seal 96 away from the flange 92 toward a second end portion 100 of the valve stem 90, and a crown 102 attached to the valve stem 90 opposite the flange 92. In one embodiment, the spring 98 is a conical spring having a base 104 that interacts with the flange 92 and an end 106 that interacts with the seal 96. The base 104 is wider than the end 106.

With reference to FIG. 3, the second end portion 100 of the valve stem 90 and the crown 102 cooperate to seal the pressurized liquid within the pressure reservoir 24 until the pads 50, 52 (FIG. 3) are touched to deform the chamber 86. The second end portion 100 and the crown 102 maintain the "primed" status of the pressure reservoir 24, which allows the user to pressurize the pressure reservoir 24 ahead of expected use of the implant 26 in its erect state. That is to say, the user may pressurize the pressure reservoir 24 to its primed state several minutes or hours or longer before "use" of the implant 26, and with one touch to the pads 50, 52, the user is able to inflate the implant 26 to achieve a nearly spontaneous erection.

FIG. 4B is a side view of the seal 96. In one embodiment, the seal 96 is a conical seal having a wider end 107 oriented toward the flange 92 and a narrower end 109 oriented toward the second end portion 100. The conical spring 98 is mated into the wider conical end 107 of the seal 96.

The wider end 107 is configured to block or deny the escape of the pressurized liquid from flowing from the pressurized implant 26 (FIG. 1) transverse through the pump body 42 and back to the pressure reservoir 24 until the pads 50, 52 (FIG. 3) are touched to deform the chamber 86. With reference to FIG. 3, the wider end 107 of the seal 96 of the transverse valve 60 is biased by the spring 98 to prevent pressurized liquid from flowing from the pressurized implant 26 into the pressure reservoir 24. The pressurized liquid in the implant 26 forces the wider end 107 of the seal 96 toward the second end portion 100 of the valve stem 90 to close off the flow path in the direction of the exhaust port 46. Thus, the implant 26 will remain pressurized and erect until the user selectively deflates the implant 26 by pumping the bulb 40.

Figure 5:
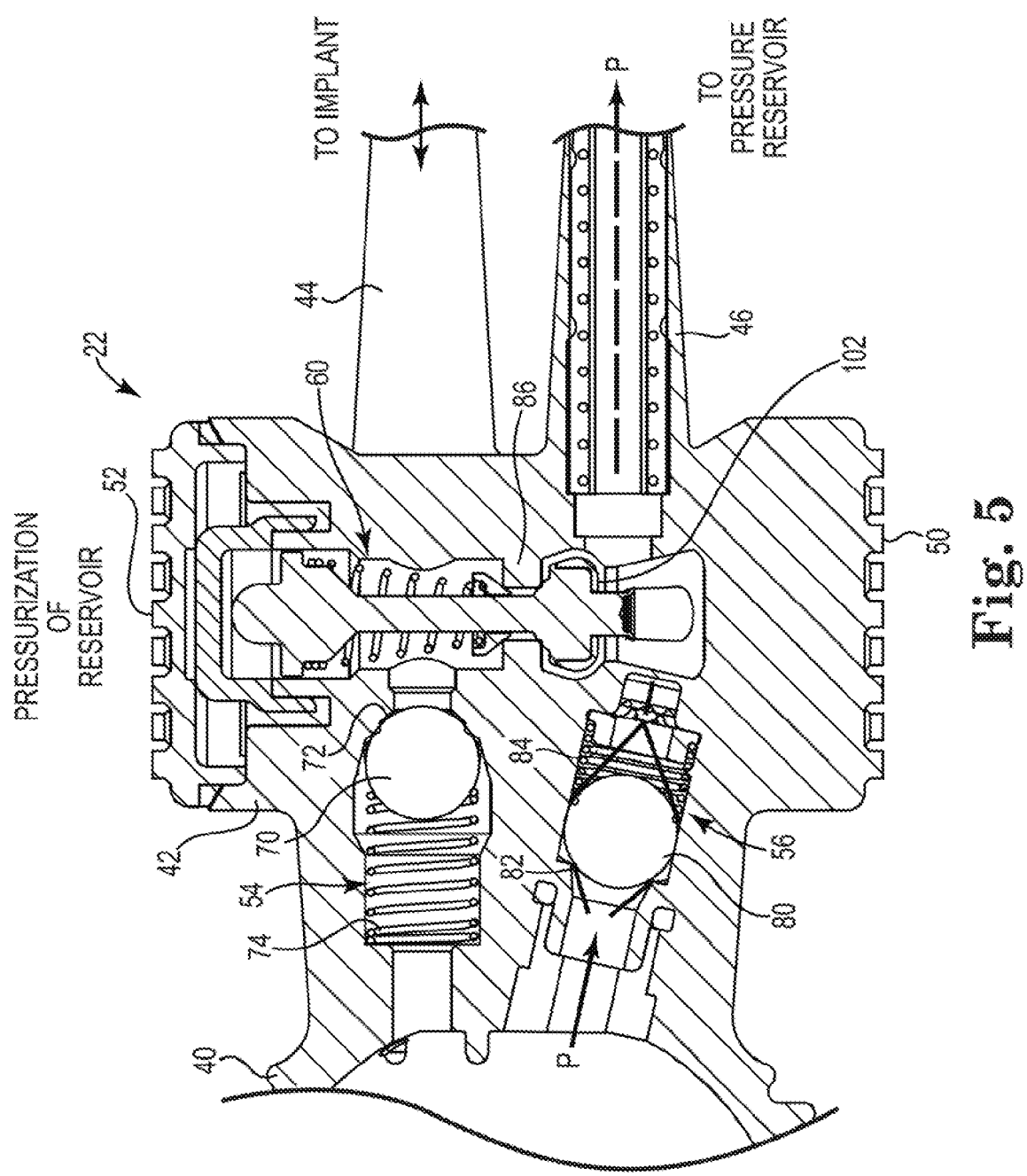
FIG. 5 is a cross-sectional view of the pump in a configuration suited to pressurize the pressure reservoir illustrated in FIG. 1.
Figure 7:
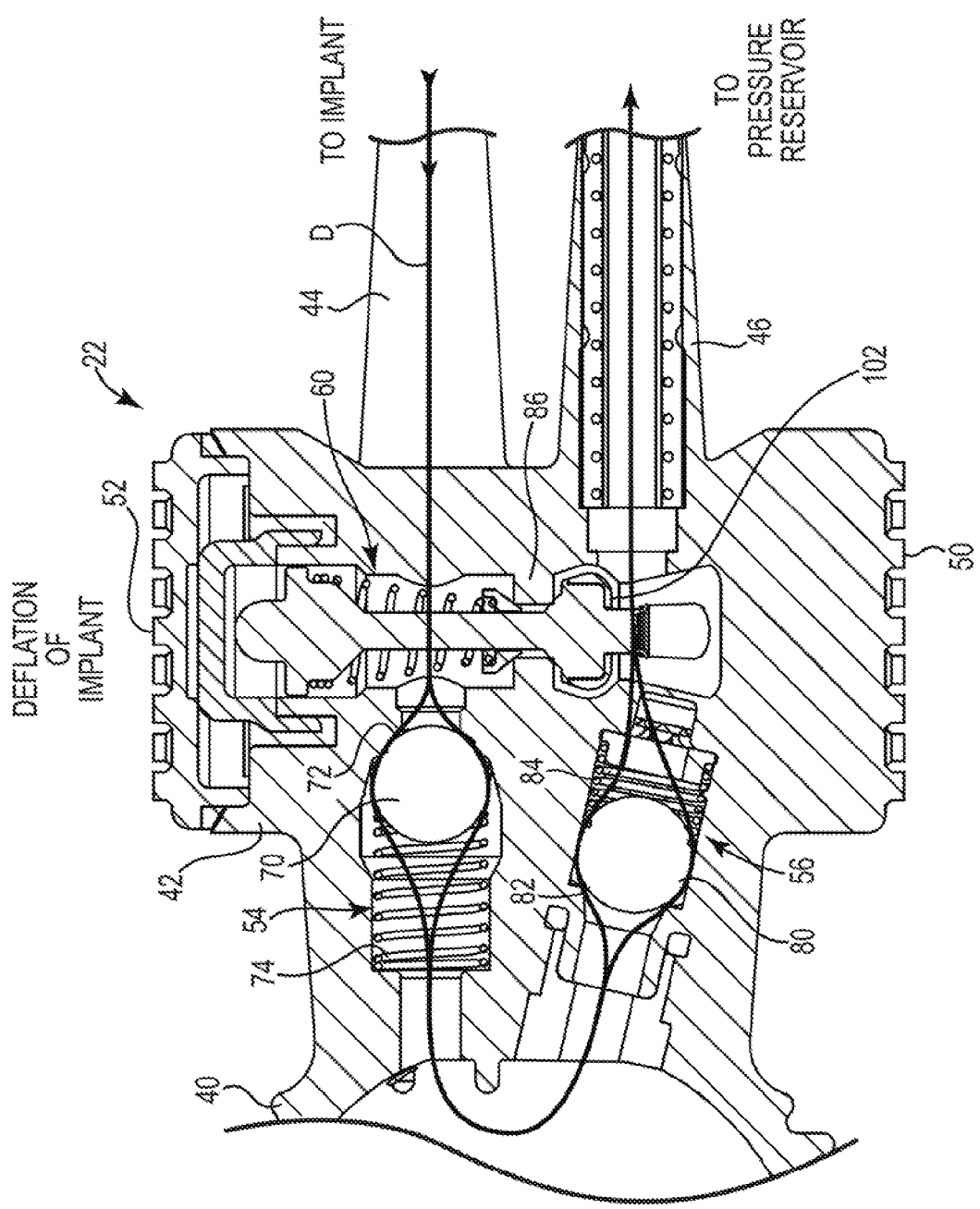
FIG. 7 is a cross-sectional view of the pump in a configuration for deflating the penile implant illustrated in FIG. 1.

FIGS. 5-7 illustrate various configurations of the pump 22. Reference is made to FIG. 1 in the following description of FIGS. 5-7.

FIG. 5 is a cross-sectional view of the pump 22 configured for pressurization of the pressure reservoir 24. Squeezing the pump bulb 40 moves the liquid in the assembly 20 into the pressure reservoir 24. When the pump bulb 40 is compressed, the liquid in the pump bulb 40 is ejected through the exhaust valve 56 along the pathway P, displacing the ball 80 away from its seat on a surface 82. The liquid is forced along the pathway P under the crown 102 of the transverse valve 60, through the exhaust port 46, and into the pressure reservoir 24.

In one embodiment, when the pump bulb 40 is squeezed, liquid moving through the exhaust valve 56 forces the crown 102 of the transverse valve 60 upward to prevent the liquid that is flowing toward the pressure reservoir 24 from being diverted transversely through the pump body 42 toward the implant 26. Subsequent multiple pumps of the pump bulb 40 pressurizes the liquid in the pressure reservoir 24. The transverse valve 60 seals off the pressurized liquid in the pressure reservoir 24 and maintains the assembly 20 in the primed status ready for immediate inflation of the implant 26. In one embodiment, the transverse valve 60 maintains the assembly 20 in the primed status with the pressure reservoir 24 pressurized above atmospheric pressure, and useful such pressures in the pressure reservoir 24 are between about 10-50 PSIg as an example.

FIG. 6 is a cross-sectional view of the pump 22 showing the configuration during immediate inflation of the implant 26. When a user desires to achieve an erection, the touch pads 50, 52 are pressed to dislodge the crown 102 (FIG. 4A) and create a liquid path around the crown 102 co-axially along the valve stem 90 and to separate the seal 96 from the chamber 86 molded around the transverse valve 60. Dislodging the seal 96 and the crown 102 provides the pressurized liquid in the pressure reservoir 24 with a pathway I through the pump body 42 that allows the pressurized liquid to flow directly into the implant 26. The tubing 30, 34 will hold a relatively small volume of liquid as compared to the pressure reservoir 24, such that the pressure in implant 26 is less than about 20-30 PSIg when the pressurized liquid occupies the implant 26. In one embodiment, the implant 26 is inflated to a pressure between 10-20 PSIg, and preferably the implant 26 is inflated to a pressure of about 15 PSIg. It has been determined that the pressure configured to inflate the penile implant to an erect state is about 10-20 PSIg.

FIG. 7 is a cross-sectional view of the pump 22 configured for deflation of implant 26. The assembly 20 allows the user to selectively deflate the implant 26 by operating the pump bulb 40. For example, when the implant 26 is an inflated (erect) state and filled with pressurized liquid, pumping the pump bulb 40 will create suction in the bulb 40 that draws the liquid from the implant 26 along the pathway D through the deflation valve 54 and into the pump bulb 40. Subsequent pumping of the bulb 40 pushes the liquid through the exhaust valve 56 back into the pressure reservoir 24. During deflation of the implant 26, the transverse valve 60 is shunted upward to block the transverse flow within the pump body 42 between the exhaust port 46 and the inflation port 44. Thus, the liquid moved through the pump bulb 40 will exit the implant 26, flow through the pump bulb 40 and under the crown 102, and back into the pressure reservoir 24.

Figure 8A:
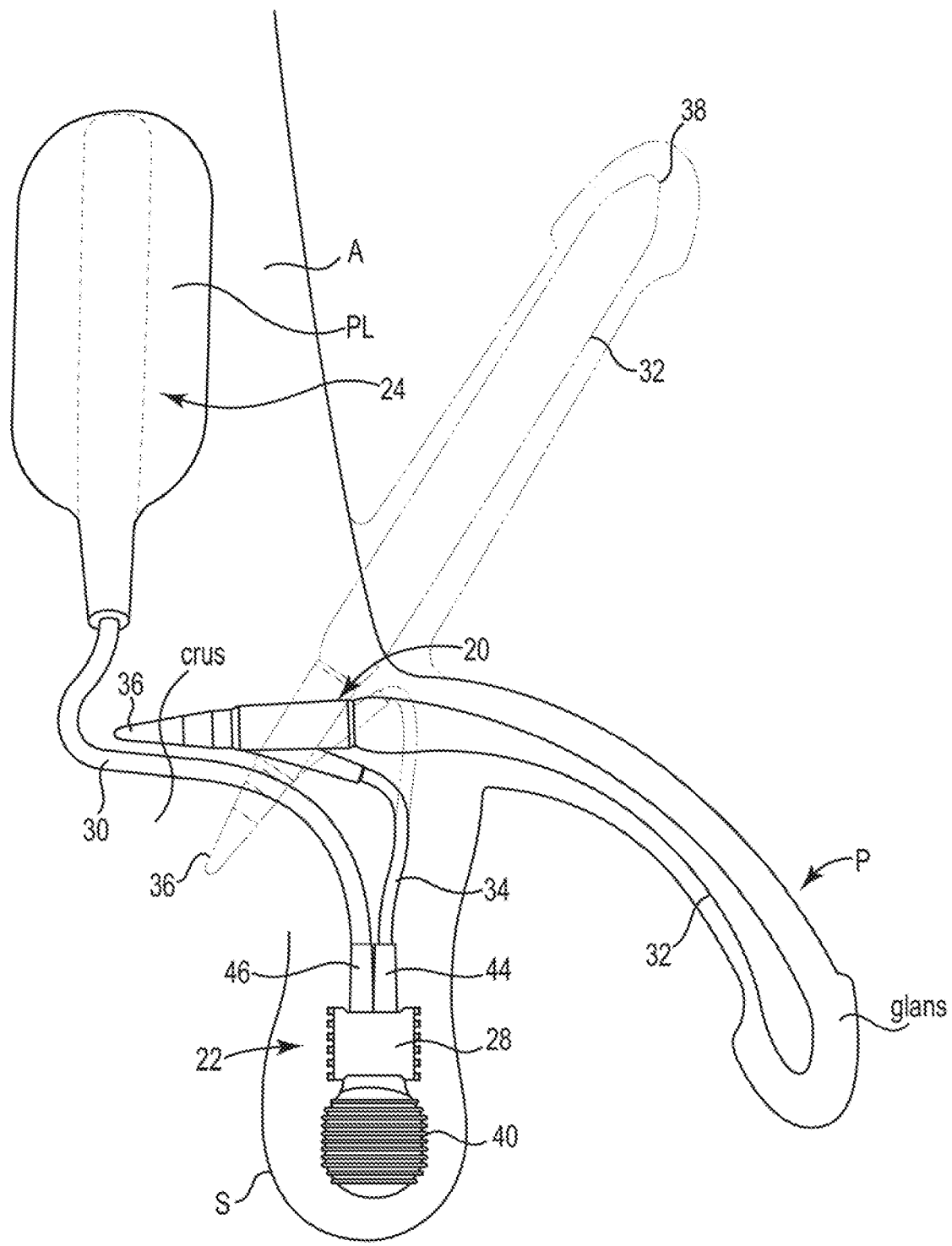
FIG. 8A is a schematic view of the body implantable penile prosthetic assembly implanted in a man.

FIG. 8A is a schematic side view of the penile prosthetic assembly 20 implanted in a user. The cylinders 32 are implanted in the penis P with the proximal end 36 inserted near the crus and the distal end 38 implanted within the glans. The reservoir 24 is implanted within the abdomen A and the pump 22 is implanted within the scrotum S. The penile prosthetic assembly 20 is operable consistent with the description above to immediately inflate the cylinders 32 by releasing pressurized liquid from the pressure reservoir 24 by activation of the release mechanism 28.

In one embodiment, the assembly 20 is implanted by the surgeon and primed by filling the pressure reservoir 24 with an appropriate volume of liquid, for example between about 100-300 ml as an example. In one embodiment, the liquid in the pressure reservoir 24 is pressurized to between about 20-50 PSIg when implanted. The assembly 20 is sealed to provide a closed system, and the pump 22 and the release mechanism 28 are employed to selectively transport the pressurized liquid in the assembly 20 between the pressure reservoir 24 and the implant 26.

In one embodiment, a method of providing a user with the inflatable penile prosthetic assembly 20 includes providing a pump 22 attachable to a pressure reservoir 24 and a penile implant 26; configuring the pressure reservoir 24 to store pressurized liquid PL; and configuring the pressure reservoir 24 to release the pressurized liquid PL from the pressure reservoir 24 to the penile implant 26 at a pressure that is configured to inflate the penile implant to an erect state.

In one embodiment, the method provides a user with an immediate erection or an erection that is spontaneous enough to mimic a natural erection. The immediate erection is achieved by first increasing pressure in the liquid in the pressure reservoir 24 to a first pressure above atmospheric pressure, for example 20-30 PSIg. This pressure level is achieved either by the surgeon initially pressurizing the reservoir 24, or later, by the user employing the pump 22 to adjust the pressure level in the pressure reservoir. This pressure level in the pressure reservoir 24 may be maintained for minutes or up to several hours or more, depending upon user preference. When the user determines that the time is appropriate to achieve an erection, the touch pads 50, 52 are activated to release the pressurized liquid PL from the pressure reservoir 24 directly into the implant 26. In one embodiment, the implant 26 is pressurized at a second pressure of about 10-20 PSIg, which is less than the pressurization of the pressure reservoir 24 (e.g., due to line losses in the assembly 20), but sufficient to maintain an erection in the implant 26.

Releasing the pressurized liquid PL from the pressure reservoir 24 into the implant 26 by touching the pads 50, 52 will result in the pressurized liquid PL moving rapidly into the implant 26. In one embodiment, the implant 26 is moved from the flaccid state to an erect state in a matter of a few seconds, for example less than about 5 seconds. The erect/inflated implant 26 is deflated by pumping the bulb 40 to transfer the liquid in the implant 26 back into the pressure reservoir 24.

FIG. 8B is a schematic graph of pressure-volume characteristics of the pressure reservoir of the body implantable penile prosthetic assembly 20 as illustrated in FIG. 8A. The pressure reservoir 24 is pressurized to a "primed" pressure condition of 30 PSIg in this example. Thus, the pressure reservoir 24 has a relatively high volume of liquid (it is essentially full) and a relatively high primed pressure of 30 PSIg. The pressurized liquid is released for the pressure reservoir 24 to the implant 26, which inflates the implant 26 to a pressure of about 15 PSIg in this example and likewise drops the pressure in the pressure reservoir 24 to about 15 PSIg. The implant 26 is deflated by pumping the bulb 40, which transfers the liquid back into the pressure reservoir 24, and with additional pumping of the bulb 40, increases the pressure in the pressure reservoir 24 back up to about 30 PSIg, as an example. Thus, the pressure reservoir 24 is not a constant pressure reservoir.

Figure 9:
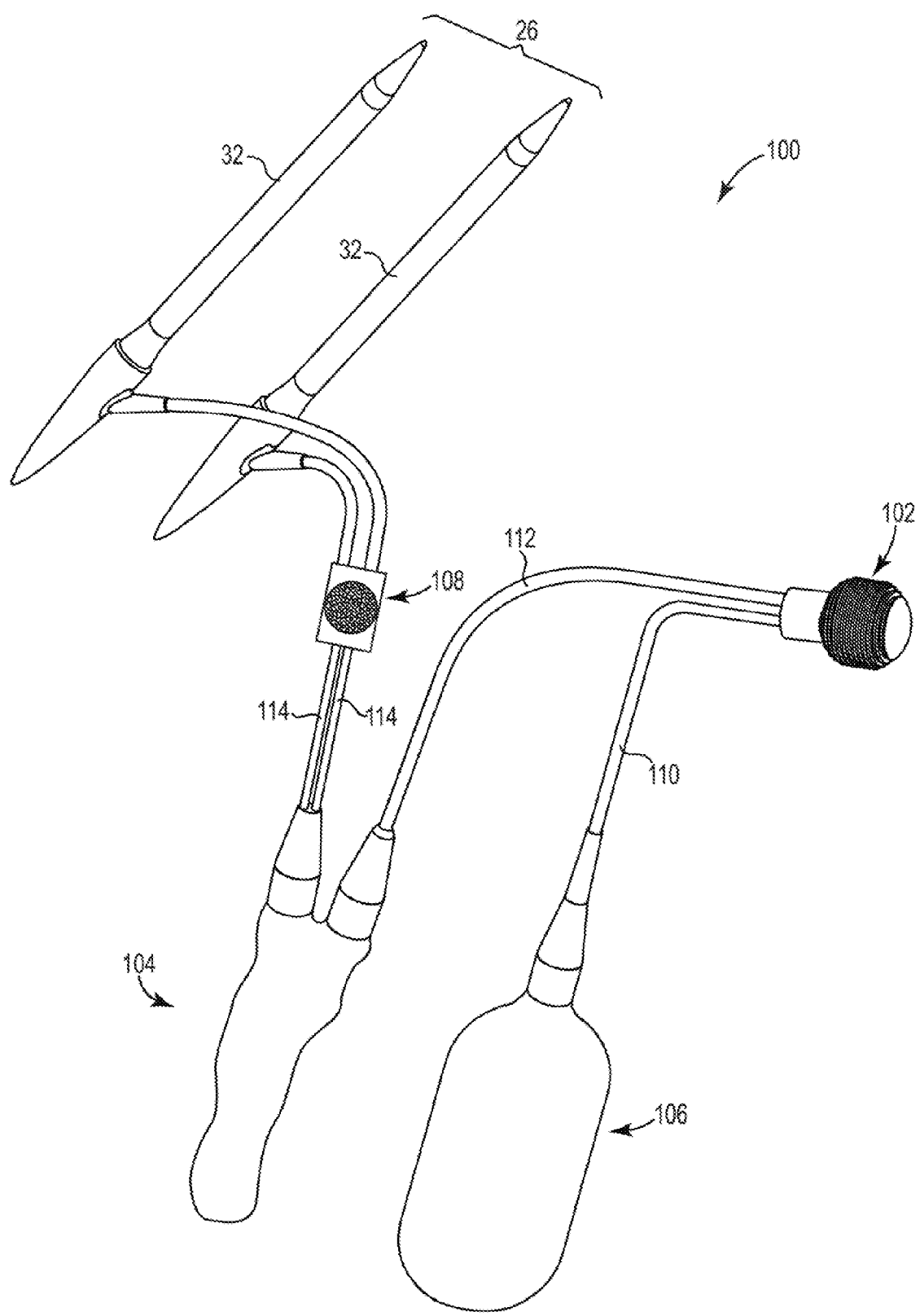
FIG. 9 is a perspective view of a body implantable penile prosthetic assembly including a pump connected between a liquid reservoir and a pressure reservoir both of which communicate with a penile implant according to one embodiment.

FIG. 9 is a perspective view of a penile prosthetic assembly 100 according to one embodiment. The penile prosthetic assembly 100 includes a pump 102 connected between a pressure reservoir 104, a liquid reservoir 106, and the penile implant 26, and has a release mechanism 108 separate from the pump 102 and connected between the pressure reservoir 104 and the penile implant 26.

The liquid reservoir 106 is shown containing an amount of liquid (i.e., inflated), and the pressure reservoir 104 and the implant 26 are shown in a deflated state. The pump 102 is provided to transfer the liquid from the liquid reservoir 106 into the pressure reservoir 104, and to additionally pressurize the liquid in the pressure reservoir 104 between 20 and 30 PSIg to provide a primed system ready for immediate inflation of the implant 26. The release mechanism 108 maintains the primed status of the system by preventing the pressurized liquid in the pressure reservoir 104 from escaping until the user initiates inflation of the implant 26. When the release mechanism 108 is activated, the pressurized liquid in the pressure reservoir 104 is released to rapidly flow into and create an erection in the implant 26.

In one embodiment, the implant 26 includes the cylinders 32 described above. A first tube 110 is connected between the liquid reservoir 106 and the pump 102, a second tube 112 is connected between the pump 102 and the pressure reservoir 104, and a pair of tubes 114 is connected between the pressure reservoir 104 and the cylinders 32. In one embodiment, a single tube connects between the pressure reservoir 104 and the release mechanism 108, and a pair of tubes extends from the release mechanism 108 to the implants 26.

Figure 10:
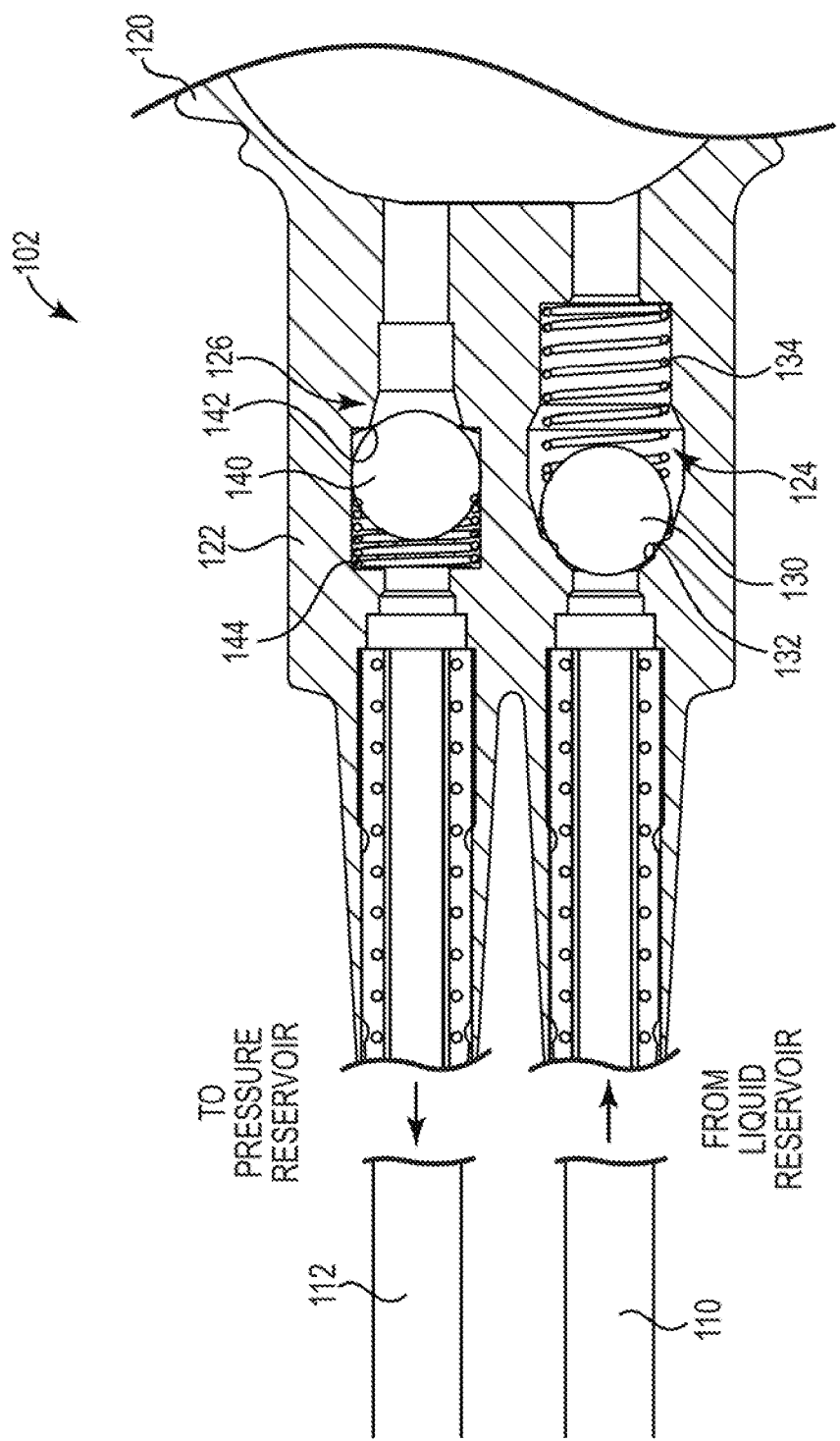
FIG. 10 is a cross-sectional view of the pump illustrated in FIG. 9.

FIG. 10 is a cross-sectional view of one embodiment of the pump 102. The pump 102 includes a pump bulb 120 connected to a pump body 122 that houses an inlet valve 124 and an outlet valve 126. In one embodiment, the pump bulb 120 and the pump body 122 are molded from a flexible polymer such as a silicone, although other polymers are also acceptable. In one embodiment, the inlet valve 124 is provided as a one-way valve including a ball 130 that is biased against a surface 132 by a spring 134. In one embodiment, the outlet valve 126 is provided as a one-way valve including a ball 140 that is biased against a surface 142 by a spring 144. The bulb 120 is operable to draw liquid from the liquid reservoir 106 through the tube 110, which displaces the ball 130 from the surface 132 and allows the liquid to flow into the bulb 120. Additional pumping of the bulb 120 pushes the ball 140 away from the surface 142 and forces the liquid through the tube 112 into the pressure reservoir 104. In one embodiment, subsequent pumping of the bulb 120 increases the pressure of the liquid in the pressure reservoir 104.

It is desirable that the assembly 100 is provided as a closed system. In one embodiment, the liquid reservoir 106 is filled with liquid (e.g., saline) and the assembly 100 is charged to an initial pressure of between 20-30 PSIg, for example. In this manner, air and other gases are sealed from the assembly 100.

In one embodiment, the pressure reservoir 104 is provided as a flexible bladder that expands when pressurized to store the potential energy of the pressurized liquid. The release mechanism 108 is provided to release the stored potential energy inside of the pressure reservoir 104, which is employed to inflate the implant 26.

Figure 11A:
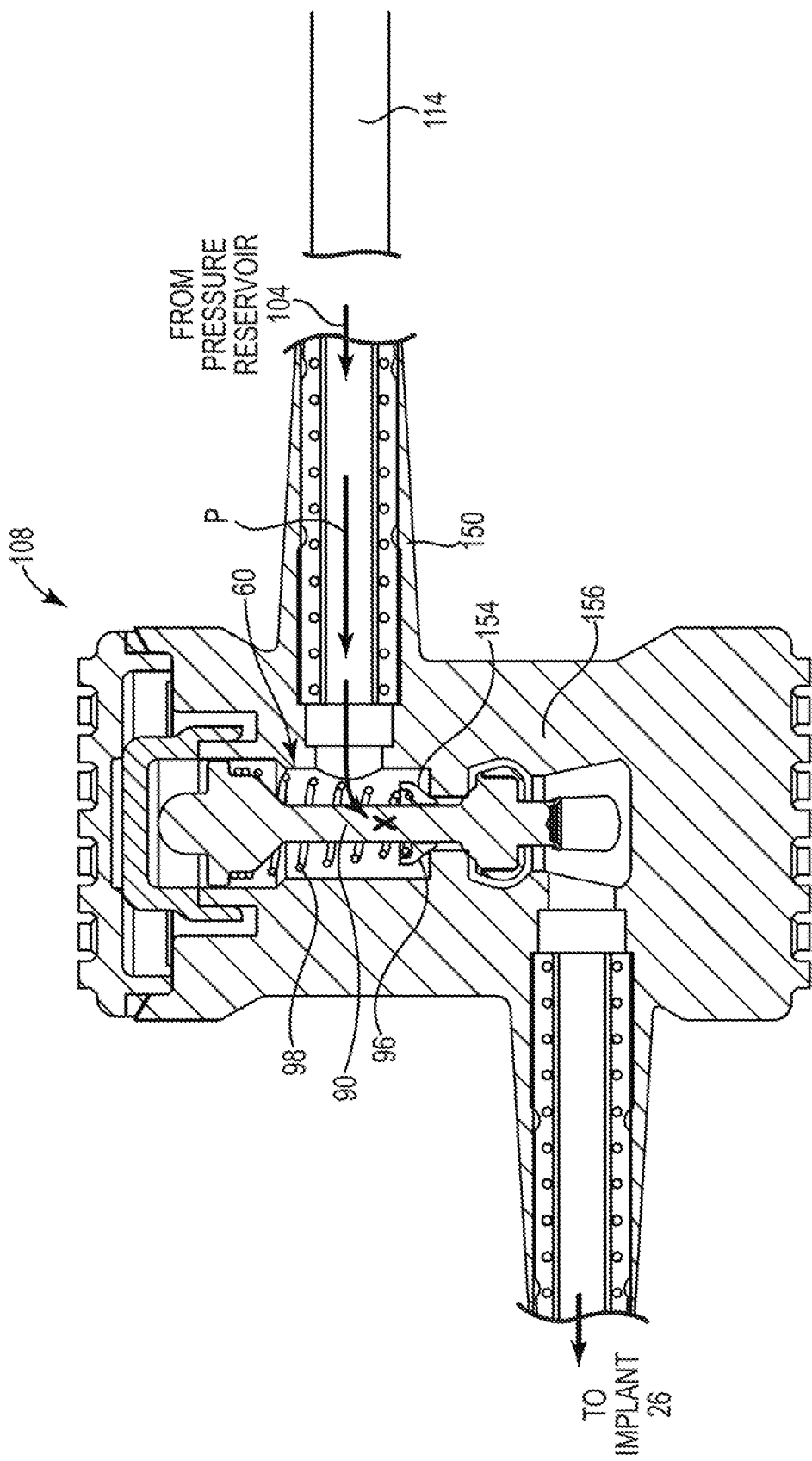
FIG. 11A is a cross-sectional view of a release mechanism of the assembly illustrated in FIG. 9.

FIG. 11A is a cross-sectional view of the release mechanism 108 closed and configured to maintain the pressure reservoir 104 in the pressurized state. In one embodiment, the release mechanism 108 includes the transverse valve 60 (as described above) positioned between an inlet port 150 that communicates with the tube 114 connected to the pressure reservoir 104 and an outlet port 152 that communicates with tubing connected to the implant 26. The transverse valve 60 is described above and functions to seal off or close the pathway of the pressurized liquid in the pressure reservoir 104 until the user activates the release mechanism 108. In particular, the transverse valve 60 is provided with the seal 96 that is biased into a closed position against a surface 154 of a chamber 156 by the spring 98. In one embodiment, the chamber 156 is flexible or deformable to allow the surface 154 to be moved away from the seal 96 to allow the pressurized liquid in the pressure reservoir 104 to flow axially along the valve stem 90 and inflate the implant 26.

Figure 11B:
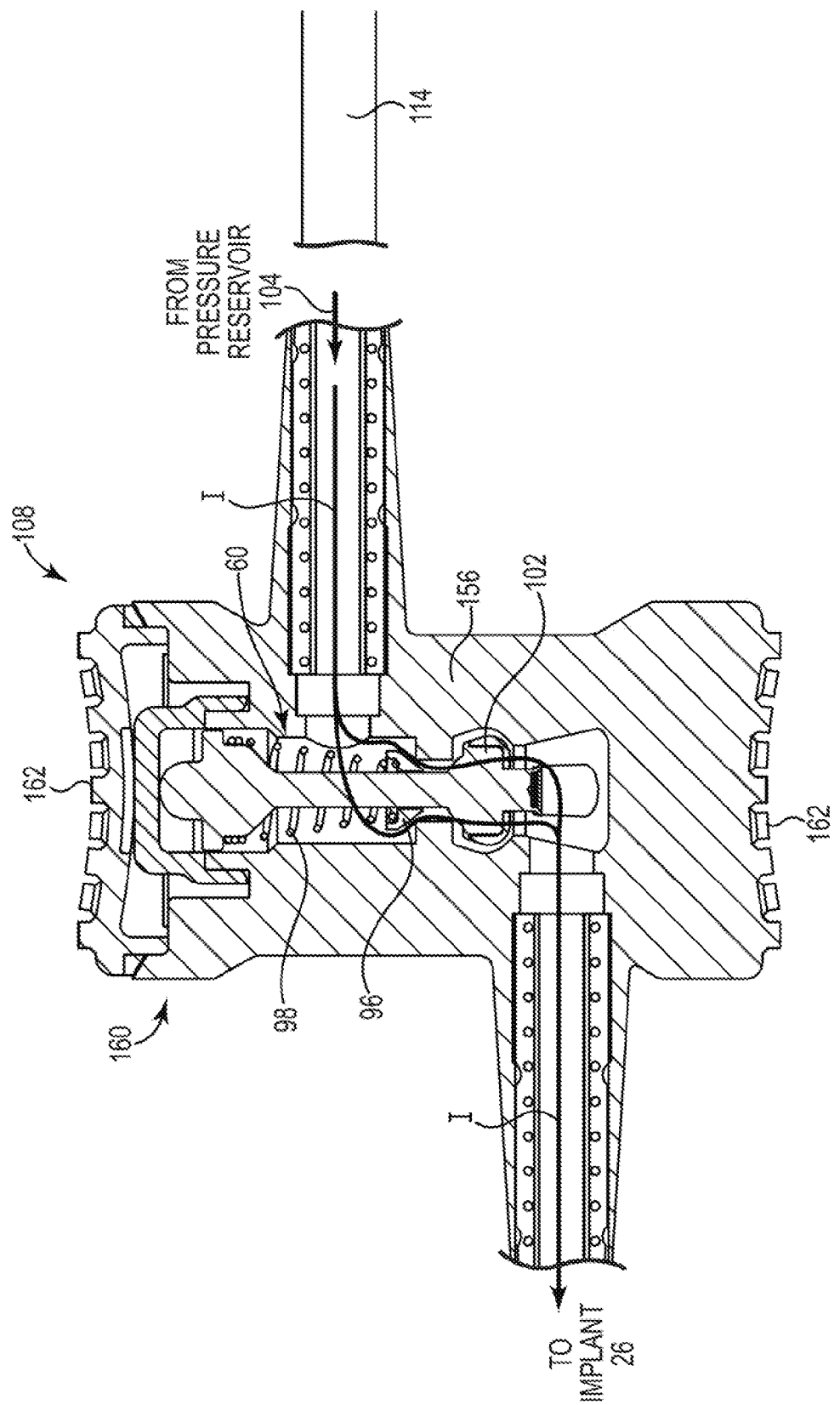
FIG. 11B is a cross-sectional view of the release mechanism illustrated in FIG. 11A in an inflation state.

FIG. 11B is a cross-sectional view of the release mechanism 108 in an inflation state. In one embodiment, the transverse valve 60 is disposed within a housing 160 provided with one or more touch pads 162. The touch pads 162 are configured to be pressed by a finger or fingers of the user to compress the housing 160 and to deform the chamber 156 such that the seal 96 is not in contact with the surface 154. The deformation in the chamber 156 provides a liquid pathway I that allows the pressurized liquid to flow from the pressure reservoir 104 directly and immediately to the implant 26. The crown 102 seals the return path to contain the pressurized liquid within the implant 26.

Embodiments of the assembly 100 allow a user of the penile implant 26 to selectively and immediately achieve an erect penis by first priming the pressure reservoir 104 of the system to an increased pressure and then subsequently releasing on demand the increased pressure from the pressure reservoir 104 to the implant 26.

Figure 12:
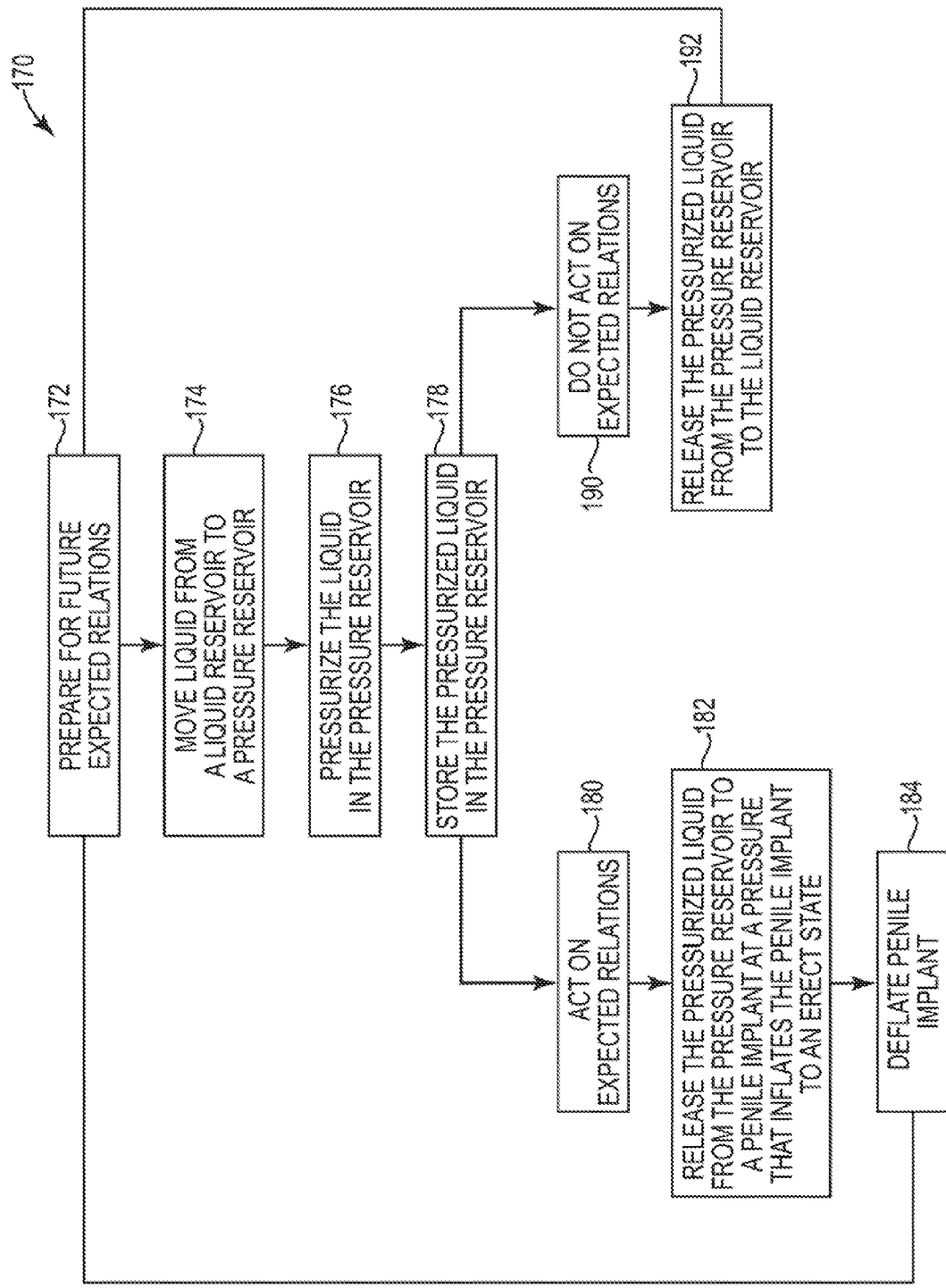
FIG. 12 is a block diagram of a method of achieving an erection in a male provided with a body implantable penile prosthetic assembly.

FIG. 12 is a block diagram 170 of a method of achieving an immediate erection in a male user provided with a body implantable penile prosthetic assembly. The method includes preparing for future expected relations at 172 and moving liquid from a liquid reservoir to pressure reservoir at 174. The method further includes pressurizing the liquid in the pressure reservoir at 176 and storing the pressurized liquid in the pressure reservoir at 178. The pressurized liquid in the pressure reservoir may be stored for several hours. When a user of the implant desires to achieve an erection, the method provides an option to act on the expected relations at 180 by releasing the pressurized liquid from the pressure reservoir to the penile implant at a pressure that inflates the implant to an erect state at 182. The method allows the user to deflate the implant at 184.

There are instances when the user, after having pressurized the pressure reservoir at 176 and storing the pressurized liquid in the pressure reservoir at 178, no longer desires to achieve an erection. The method provides the user with the option to not act on expected relations at 190 by releasing the pressurized liquid from the pressure reservoir back to the liquid reservoir at 192.

FIG. 13 is a perspective view of the penile prosthetic assembly 100 showing the liquid reservoir 106 deflated after the liquid in the reservoir 106 has been moved into the pressure reservoir 104 (now inflated). The implant 26 remains in a deflated state.

Figure 14:
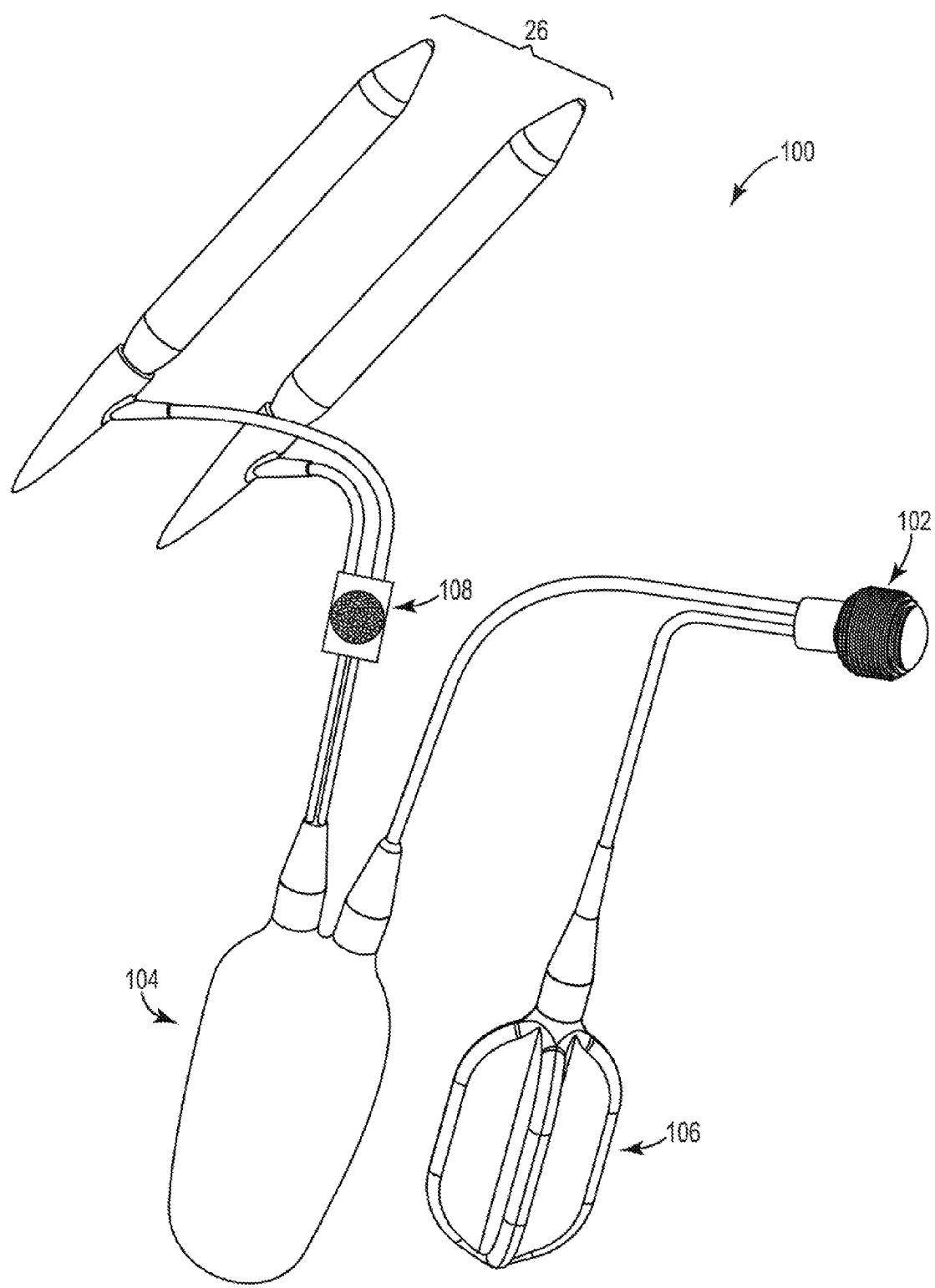
FIG. 14 is a perspective view of the body implantable penile prosthetic assembly illustrated in FIG. 9 with the pressure reservoir depressurized and the penile implant inflated according to one embodiment.

FIG. 14 is a perspective view of the penile prosthetic assembly 100 showing the liquid reservoir 106 deflated after emptying its contents into the pressure reservoir 104, and the liquid pressure between the pressure reservoir 104 and the implant 26 equalized, which partially deflates the pressure reservoir 104 and fully inflates the implants 26

Figure 15:
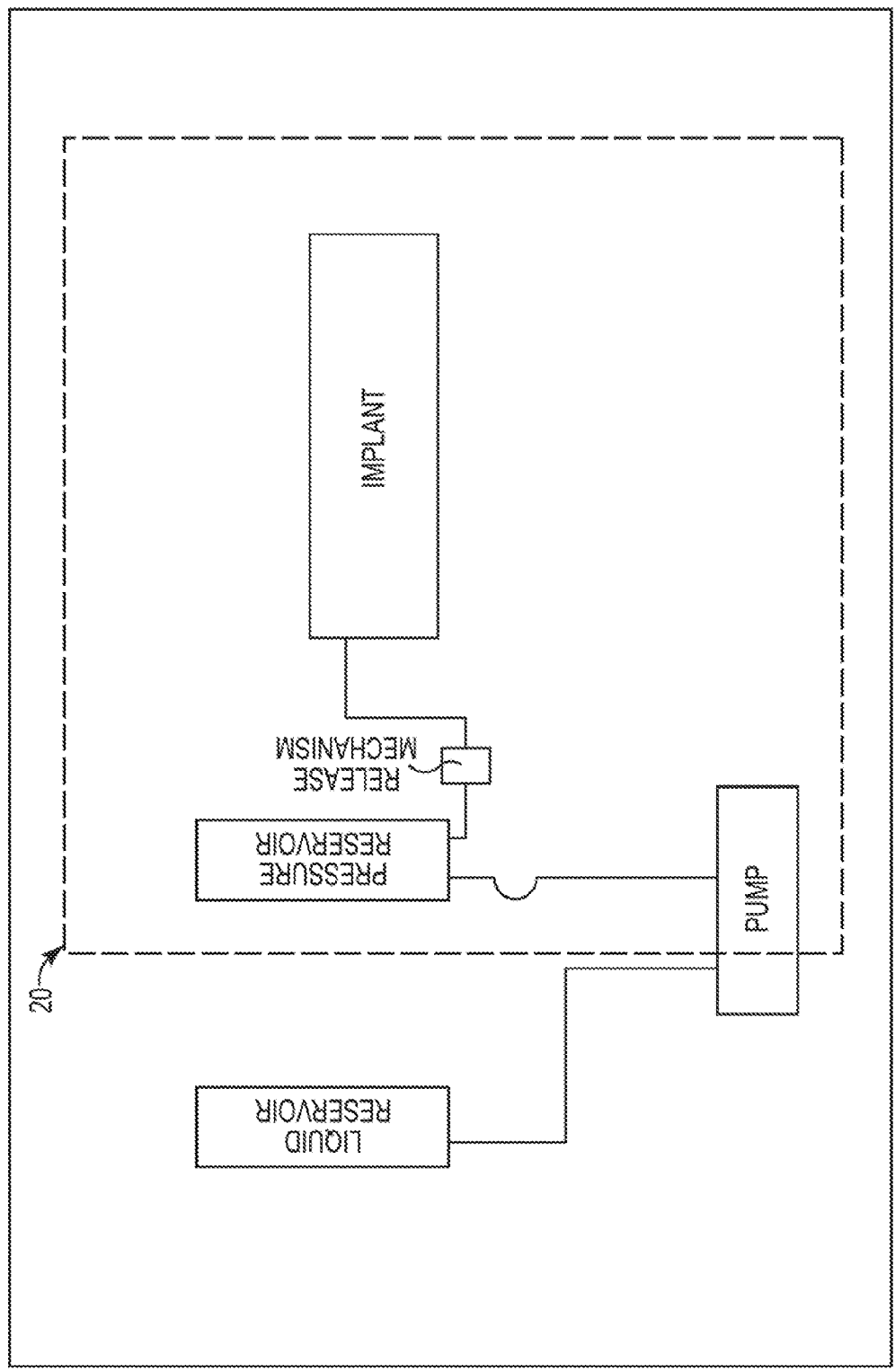
FIG. 15 is a schematic view of two embodiments of a body implantable penile prosthetic assembly.

FIG. 15 is a schematic view of the relationship between the body implantable penile prosthetic assembly 20 (FIG. 1) and the body implantable penile prosthetic assembly 100 (FIG. 9) according to one embodiment. The assembly 100 includes the liquid reservoir 106 and provides the pump 102 that transfers the liquid from the liquid reservoir 106 into the pressure reservoir 104. In contrast, the assembly 20 of FIG. 1 includes the pressure reservoir 24 containing a volume of pressurized liquid and a release mechanism 28 that releases the pressurized liquid from the pressure reservoir 24 to the implant 26. In this sense, the assembly 20 is a subset of the assembly 100, where both assemblies 20, 100 provide a solution for erectile dysfunction.

Figure 16:
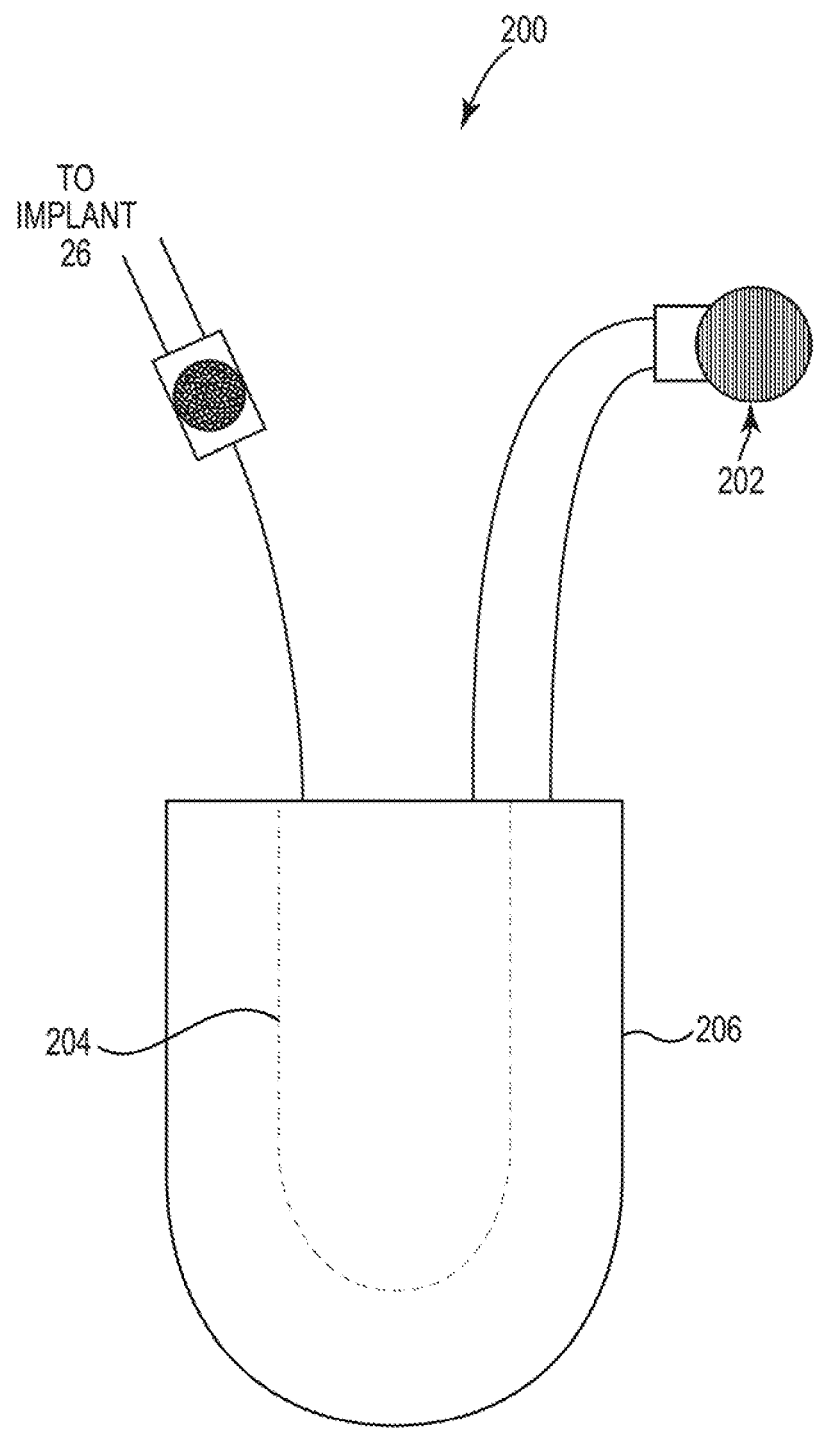
FIG. 16 is a side view of a pressure reservoir disposed inside of a liquid reservoir according to one embodiment of a body implantable penile prosthetic assembly.

FIG. 16 is a side view of one embodiment of a penile prosthetic assembly 200 including a pump 202 connected to a pressure reservoir 204 that is disposed inside of a liquid reservoir 206, and having a release mechanism 208 connected between the pressure reservoir 204 and the penile implant 26.

Figure 17:
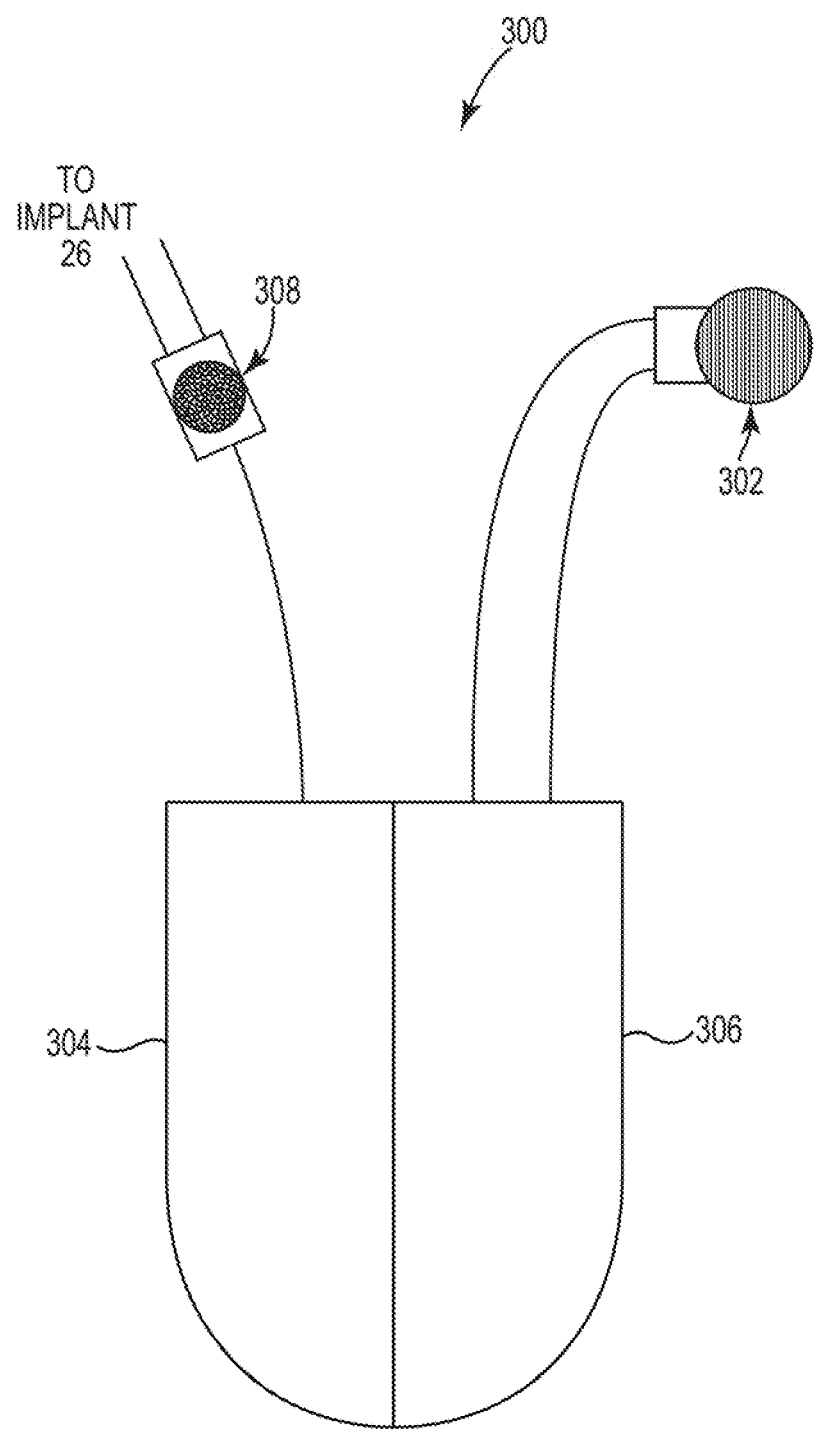
FIG. 17 is a side view of a pressure reservoir connected side-by-side to a liquid reservoir according to one embodiment of a body implantable penile prosthetic assembly.

FIG. 17 is a side view of one embodiment of the penile prosthetic assembly 300 including a pump 302 connected to a pressure reservoir 304 that is connected to a side of the liquid reservoir 306, and having a release mechanism 308 connected between the pressure reservoir 304 and the penile implant 26.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. A body implantable penile prosthetic assembly offering a user a one touch to erection (OTTER) capability and a penile implant deflation capability, the assembly comprising:
   a pump configured to be connected to a pressure reservoir and a penile implant, the pump operable to pressurize liquid in the pressure reservoir and the pressure reservoir operable to store the pressurized liquid at a first pressure between 20-50 PSIg that is configured to inflate the penile implant to an erect state; and
   a release mechanism configured to be connected between the pressure reservoir and the penile implant, the release mechanism operable to inflate the penile implant with one-touch input from the user where the release mechanism is configured to release the stored pressurized liquid from the pressure reservoir to inflate the penile implant at a second pressure between 10-20 PSIg.

2. The assembly of claim 1, wherein the release mechanism is integrated with the pump.

3. The assembly of claim 1, wherein the pump includes a deflation mechanism that is operable to deflate the penile implant and transfer the pressurized liquid from the penile implant to the pressure reservoir.

4. The assembly of claim 3, wherein the deflation mechanism is a valve integrated in the pump.

5. The assembly of claim 4, wherein the release mechanism comprises a transverse valve that is disposed in the pump transverse to a longitudinal axis of the deflation mechanism and a seal that is biased to retain the pressurized liquid in the pressure reservoir.

6. The assembly of claim 5, wherein a body of the pump is deformable to displace the seal to allow the pressurized liquid in the pressure reservoir to flow co-axially alongside the transverse valve to the penile implant.

7. The assembly of claim 1, wherein the penile prosthetic assembly is sealed when implanted to obviate adding additional liquid, and the pressure reservoir comprises walls that are configured expand to store potential energy created when the pump increases pressure of the liquid in the pressure reservoir.

8. The assembly of claim 1, wherein the pump comprises a touch pad that is operable to provide the user with the one touch to erection (OTTER) capability.

9. The assembly of claim 1, wherein the pump further comprises:
   an exhaust valve and a bulb operable to move liquid through the exhaust valve to the pressure reservoir and pressurize the pressurized liquid in the pressure reservoir.

10. The assembly of claim 1, further comprising:
   a liquid reservoir configured to be connected between the pump and the pressure reservoir, the pump configured to transfer liquid from the liquid reservoir to the pressure reservoir and pressurize the liquid transferred into the pressure reservoir.

11. The assembly of claim 10, wherein the pressure reservoir is attached to a side of the liquid reservoir.

12. The assembly of claim 10, wherein the pressure reservoir is disposed inside of the liquid reservoir.

13. The assembly of claim 1, wherein the pressure reservoir comprises a flexible bladder.

14. A body implantable penile prosthetic assembly comprising:
   a pump having a one touch to erection (OTTER) capability and a penile implant deflation capability, the pump configured to be connected to a pressure reservoir and a penile implant that is inflatable with one-touch input from the user, the pump operable to pressurize liquid in the pressure reservoir and the pressure reservoir operable to store the pressurized liquid at a first pressure between 20-50 PSIg that is configured to inflate the penile implant to an erect state;
   a release mechanism integrated into the pump and configured to release the stored pressurized liquid from the pressure reservoir to inflate the penile implant at a second pressure between 10-20 PSIg; and
   a deflation mechanism integrated into the pump and operable to deflate the penile implant and transfer the pressurized liquid from the penile implant to the pressure reservoir.

* * * * *